(12) United States Patent
Jakobsen et al.

(10) Patent No.: US 8,378,074 B2
(45) Date of Patent: Feb. 19, 2013

(54) HIGH AFFINITY HIV T CELL RECEPTORS

(75) Inventors: Bent Karsten Jakobsen, Abingdon (GB); Yi Li, Abingdon (GB); Steven Mark Dunn, Abingdon (GB); Peter Eamon Molloy, Abingdon (GB)

(73) Assignee: Immunocore Limited (GB)

( * ) Notice: Subject to any disclaimer, the term of this patent is extended or adjusted under 35 U.S.C. 154(b) by 979 days.

(21) Appl. No.: 11/887,536

(22) PCT Filed: Mar. 29, 2006

(86) PCT No.: PCT/GB2006/001147
§ 371 (c)(1),
(2), (4) Date: Nov. 7, 2008

(87) PCT Pub. No.: WO2006/103429
PCT Pub. Date: Oct. 5, 2006

(65) Prior Publication Data
US 2009/0214551 A1    Aug. 27, 2009

(30) Foreign Application Priority Data

Apr. 1, 2005  (GB) .................................. 0506760.8
Aug. 10, 2005 (GB) .................................. 0516487.6

(51) Int. Cl.
*C07K 1/00*      (2006.01)
*C07K 14/00*     (2006.01)
*C07K 17/00*     (2006.01)

(52) U.S. Cl. ........................................ 530/350

(58) Field of Classification Search .................. None
See application file for complete search history.

(56) References Cited

U.S. PATENT DOCUMENTS

2002/0058253 A1* 5/2002 Kranz et al. .................... 435/6

FOREIGN PATENT DOCUMENTS

| WO | WO 03/020763 A  | 3/2003  |
| WO | WO 2004/044004 A | 5/2004  |
| WO | WO 2005/114215 A | 12/2005 |

OTHER PUBLICATIONS

Portolano et al., 1993, J. Immunol. vol. 150: 880-887.*
Brawley et al., 2002, J. Immunol. vol. 168: 3894-3901.*
Chervin et al., 2008, J. Immunol. Methods. vol. 339: 175-184.*
Kieke et al., 1999, PNAS vol. 96: 5651-5656.*
Brawley et al., 1999, J. immunol. vol. 163: 4946-4952.*
Goyarts et al., 1998, Mol. Immunol. vol. 35: 593-607.*
Grant et al., 2002, J. Immunol. vol. 168: 3933-3940.*
Anikeeva et al.; "Soluble HIV-specific T cell receptor: expression, purification and analysis of the specificity"; Journal of Immunological Methods, vol. 277, No. 1-2, Jun. 1, 2003, pp. 75-86, XP004430548.
Li Yi et al.; "Directed evolution of human T-cell receptors with picomolar affinities by phage display", Nature Biotechnology, vol. 23, No. 3, Mar. 2005, pp. 349-354, XP002336795. (published on line Feb. 20, 2005).
Holler et al.; "In vitro evolution of a T cell receptor with high affinity for peptide/MHC", Proceedings of the National Academy of Sciences of USA, vol. 97, No. 10, May 9, 2000, pp. 5387-5392, XP002217232. (published on line Apr. 25, 2000).
Anikeeva et al.; "Distinct molecular mechanisms account for the specificity of two different T-cell receptors"; Biochemistry, Apr. 29, 2003, vol. 42, No. 16, Apr. 29, 2003, pp. 4709-4716, XP002407870. (published on line Apr. 1, 2003).
Iversen et al.; "Conflicting selective forces affect T cell receptor contacts in an immunodominant human immunodeficiency virus epitope", Nature Immunology, Feb. 2006, vol. 7, No. 2, pp. 179-189, XP002407871.(published on line Jan. 1, 2006).

* cited by examiner

Primary Examiner — Amy Juedes
(74) Attorney, Agent, or Firm — Vedder Price P.C.; Thomas J. Kowalski; Smitha B. Uthaman

(57) ABSTRACT

The present invention provides TCRs having high affinity. The TCR binds to SLYNTVATL (SEQ ID NO:16)-HLA-A*0201 with a $K_D$ of less than or equal to 1 μM and/or an off-rate ($k_{off}$) of $1 \times 10^{-3}$ $S^{-1}$ or slower using Surface Plasmon Resonance. The TCRs are non-native, isolated or recombinant. The TCRs are useful, either alone, or with a therapeutic agent, for targeting HIV infected cells that present the SLYNTVATL (SEQ ID NO:16)-HLA-A*0201 complex.

24 Claims, 24 Drawing Sheets

Figure 1a

```
                10                          20
                *                           *
    M A Q K E V E Q N S G P L S V P E G A I A S L N C T Y S D 30                 40                  50
       *                  *                   *
    R G S Q S F F W Y R Q Y S G K S P E L I M F I Y S N G D K 60                  70                  80
          *                   *                   *
    E D G R F T A Q L N K A S Q Y I S L L I R D S K L S D S A 90                 100                 110
            *                   *                   *
    T Y L C A V R T N S G Y A L N F G K G T S L L V T P H
```
(SEQ ID No: 1)

Figure 1b

```
          10                  20
           *                   *
M E A G V T Q S P T H L I K T R G Q Q V T L R C S P K S G 30                  40                  50
  *                   *                   *
H D T V S W Y Q Q A L G Q G P Q F I F Q Y Y E E E E R Q R 60                  70                  80
    *                   *                   *
G N F P D R F S G H Q F P N Y S S E L N V N A L L L G D S 90                 100                 110
    *                   *                   *
A L Y L C A S S D T V S Y E Q Y F G P G T R L T V T
```
(SEQ ID NO: 2)

Figure 2a atggcccagaaggaggtggagcagaattctggaccccctcagtgttccagagggagccattgcctctctcaattgcacttaca
gtgaccgaggttcccagtccttcttctggtacagacaatattctgggaaaagccctgagttgataatgttcatatactccaatgg
tgacaaagaagatggaaggtttacagcacagctcaataaagccagccagtatatttccctgctcatcagagactccaagctc
agtgattcagccacctacctctgtgcggtgcgcacaaattcgggtatgcactcaacttcggcaaaggcacctcgctgttggt
cacaccccatatccagaaccctgaccctgccgtgtaccagctgagagactctaaatccagtgacaagtctgtctgcctattca
ccgattttgattctcaaacaaatgtgtcacaaagtaaggattctgatgtgtatatcacagacaaaactgtgctagacatgaggtc
tatggacttcaagagcaacagtgctgtggcctggagcaacaaatctgactttgcatgtgcaaacgccttcaacaacagcatta
ttccagaagacaccttcttccccagcccagaaagttcctaa
(SEQ ID No: 3)

Figure 2b atggaggctggagtcacacaaagtcccacacacctgatcaaaacgagaggacagcaagtgactctgagatgctctcctaa
gtctgggcatgacactgtgtcctggtaccaacaggccctgggtcaggggccccagtttatctttcagtattatgaggaggaag
agagacagagaggcaacttccctgatcgattctcaggtcaccagttccctaactatagctctgagctgaatgtgaacgccttg
ttgctgggggactcggccctctatctctgtgccagcagcgacaccgtctcctacgagcagtacttcgggccggggcaccagg
ctcacggtcacagaggacctgaaaaacgtgttcccacccgaggtcgctgtgtttgagccatcagaagcagagatctcccac
acccaaaaggccacactggtgtgcctggccacaggcttctaccccgaccacgtggagctgagctggtgggtgaatgggaa
ggaggtgcacagtggggtcagcacagacccgcagcccctcaaggagcagcccgccctcaatgactccagatacgctctg
agcagccgcctgagggtctcggccaccttctggcaggaccccgcaaccacttccgctgtcaagtccagttctacgggctc
tcggagaatgacgagtggacccaggatagggccaaacccgtcacccagatcgtcagcgccgaggcctggggtagagca
gactaa (SEQ ID No: 4)

Figure 3a

```
M A Q K E V E Q N S G P L S V P E G A I A S L N C T Y S D R G S Q S F
F W Y R Q Y S G K S P E L I M F I Y S N G D K E D G R F T A Q L N K A
S Q Y I S L L I R D S K L S D S A T Y L C A V R T N S G Y A L N F G K
G T S L L V T P H I Q N P D P A V Y Q L R D S K S S D K S V C L F T D
F D S Q T N V S Q S K D S D V Y I T D K T V L D M R S M D F K S N S A
V A W S N K S D F A C A N A F N N S I I P E D T F F P S P E S S
```
(SEQ ID No: 5)

Figure 3b

```
M E A G V T Q S P T H L I K T R G Q Q V T L R C S P K S G H D T V S W
Y Q Q A L G Q G P Q F I F Q Y Y E E E E R Q R G N F P D R F S G H Q F
P N Y S S E L N V N A L L L G D S A L Y L C A S S D T V S Y E Q Y F G
P G T R L T V T E D L K N V F P P E V A V F E P S E A E I S H T Q K A
T L V C L A T G F Y P D H V E L S W W V N G K E V H S G V S T D P Q P
L K E Q P A L N D S R Y A L S S R L R V S A T F W Q D P R N H F R C Q
V Q F Y G L S E N D E W T Q D R A K P V T Q I V S A E A W G R A D
```
(SEQ ID No: 6)

Figure 4a ccatcgatggcccagaaggaggtggagcagaattctggaccccctcagtgttccagagggagccattgcctctctcaattgc
acttacagtgaccgaggttcccagtccttcttctggtacagacaatattctgggaaaagccctgagttgataatgttcatatactc
caatggtgacaaagaagatggaaggtttacagcacagctcaataaagccagccagtatatttccctgctcatcagagactcc
aagctcagtgattcagccacctacctctgtgcggtgcgcacaaattccgggtatgcactcaacttcggcaaaggcacctcgc
tgttggtcacaccccatatccagaaccctgaccctgccgtgtaccagctgagagactctaagtcgagtgacaagtctgtctgc
ctattcaccgatttttgattctcaaacaaatgtgtcacaaagtaaggattctgatgtgtatatcacagacaaatgtgtgctagacat
gaggtctatggacttcaagagcaacagtgctgtggcctggagcaacaaatctgactttgcatgtgcaaacgccttcaacaac
agcattattccagaagacaccttcttccccagcccagaaagttcctaa
(SEQ ID No: 7)

Figure 4b tctctcattaatggaggctggagtcacacaaagtcccacacacctgatcaaaacgagaggacagcaagtgactctgagatg
ctctcctaagtctgggcatgacactgtgtcctggtaccaacaggccctgggtcaggggccccagtttatctttcagtattatga
ggaggaagagagacagagaggcaacttccctgatcgattctcaggtcaccagttccctaactatagctctgagctgaatgtg
aacgccttgttgctgggggactcggccctctatctctgtgccagcagcgacaccgtctcctacgagcagtacttcgggccgg
gcaccagg
ctcacggtcacagaggacctgaaaaacgtgttcccacccgaggtcgctgtgtttgagccatcagaagcagagatctcccac
acccaaaaggccacactggtgtgcctggccaccggtttctaccccgaccacgtggagctgagctggtgggtgaatgggaa
ggaggtgcacagtggggtctgcacagacccgcagcccctcaaggagcagcccgccctcaatgactccagatacgctctg
agcagccgcctgagggtctcggccaccttctggcaggaccccgcaaccacttccgctgtcaagtccagttctacgggctc
tcggagaatgacgagtggacccaggatagggccaaacccgtcacccagatcgtcagcgccgaggcctggggtagagca
gactaa
(SEQ ID No: 8)

Figure 5a

M A Q K E V E Q N S G P L S V P E G A I A S L N C T Y S D R G S Q S F
F W Y R Q Y S G K S P E L I M F I Y S N G D K E D G R F T A Q L N K A
S Q Y I S L L I R D S K L S D S A T Y L C A V R T N S G Y A L N F G K
G T S L L V T P H I Q N P D P A V Y Q L R D S K S S D K S V C L F T D
F D S Q T N V S Q S K D S D V Y I T D K C V L D M R S M D F K S N S A
V A W S N K S D F A C A N A F N N S I I P E D T F F P S P E S S (SEQ ID No: 9)

Figure 5b

M E A G V T Q S P T H L I K T R G Q Q V T L R C S P K S G H D T V S W
Y Q Q A L G Q G P Q F I F Q Y Y E E E E R Q R G N F P D R F S G H Q F
P N Y S S E L N V N A L L L G D S A L Y L C A S S D T V S Y E Q Y F G
P G T R L T V T E D L K N V F P P E V A V F E P S E A E I S H T Q K A
T L V C L A T G F Y P D H V E L S W W V N G K E V H S G V C T D P Q P
L K E Q P A L N D S R Y A L S S R L R V S A T. F W Q D P R N H F R C Q
V Q F Y G L S E N D E W T Q D R A K P V T Q I V S A E A W G R A D (SEQ ID No: 10)

Figure 6a

M A Q K E V E Q N S G P L S V P E G A I A S L N C T Y S D R
G S Q S F F W Y R Q Y S G K S P E L I M F I Y S N G D K E D
G R F T A Q L N K A S Q Y I S L L I R D S K L S D S A T Y L
C A V R S̲ A H̲ G Y S̲ L N F G K G T S L L V T P H
(SEQ ID NO: 11)

Figure 6b

M A Q K E V E Q N S G P L S V P E G A I A S L N C T Y S D R
G S Q S F F W Y R Q Y S G K S P E L I M F I Y S N G D K E D
G R F T A Q L N K A S Q Y I S L L I R D S K L S D S A T Y L
C A V R S̲ A H̲ G Y A L N F G K G T S L L V T P H
(SEQ ID NO: 12)

Figure 6c

M A Q K E V E Q N S G P L S V P E G A I A S L N C T Y S D R
G S Q S F F W Y R Q Y S G K S P E L I M F I Y S N G D K E D
G R F T A Q L N K A S Q Y I S L L I R D S K L S D S A T Y L
C A V R G̲ A H̲ D Y A L N F G K G T S L L V T P H
(SEQ ID NO: 13)

Figure 7a

M E A G V T Q S P T H L I K T R G Q Q V T L R C S P K S G H
D T V S W Y Q Q A L G Q G P Q F I F Q Y <u>V R G V</u> E R Q R G N
F P D R F S G H Q F P N Y S S E L N V A L L L G D S A L Y
L C A S S D T V S Y E Q Y F G P G T R L T V T (SEQ ID NO: 14)

Figure 7b

M E A G V T Q S P T H L I K T R G Q Q V T L R C S P K S G H
D T V S W Y Q Q A L G Q G P Q F I F Q Y <u>A L G E</u> E R Q R G N
F P D R F S G H Q F P N Y S S E L N V A L L L G D S A L Y
L C A S S D T V S Y E Q Y F G P G T R L T V T (SEQ ID NO: 15)

Figure 8a

I Q N P D P A V Y Q L R D S K S S D K S V C L F T
D F D S Q T N V S Q S K D S D V Y I T D K
(SEQ ID NO: 19)

Figure 8b

E D L N K V F P P E V A V F E P S E A E I S H T Q K A T
L V C L A T G F F P D H V E L S W W V N G K E V H S G V
(SEQ ID NO: 20)

Figure 8c

E D L K N V F P P E V A V F E P S E A E I S H T Q K A T
L V C L A T G F Y P D H V E L S W W V N G K E V H S G V
(SEQ ID NO: 21)

Figure 9

PEX954 gatctcgatcccgcgaaattaatacgactcactatagggagaccacaacggtttccctctagaaataattttgtttaactttaaga
aggagatataatcgatgtctaactcgagtgacaagtctgtctgcctattcaccgattttgattctcaaacaaatgtgtcacaaagt
aaggattctgatgtgtatatcacagacaaatgtgtgctagacatgaggtctatggacttcaagagcaacagtgctgtggcctg
gagcaacaaatctgactttgcatgtgcaaacgccttcaacaacagcattattccagaagacaccttcttccccagcccagaaa
gttcctaagcttgaattccgatccggctgctaacaaagcccgaaaggaagctgagttggctgctgccaccgctgagcaataa
ctagcataacccttggggcctctaaacgggtcttgaggggttttttgctgaaaggaggaactatatccggataattcttgaag
acgaaagggcctcgtgatacgcctatttttataggttaatgtcatgataataatggtttcttagacgtgaggtggcacttttcggg
gaaatgtgcgcggaaccctatttgtttatttttctaaatacattcaaatatgtatccgctcatgagacaataaccctgataaatgc
ttcaataatattttgttaaaattcgcgttaaattttgttaaatcagctcatttttaaccaataggccgaaatcggcaaaatcccttat
aaatcaaaagaatagaccgagatagggttgagtgttgttccagtttggaacaagagtccactattaaagaacgtggactccaa
cgtcaaagggcgaaaaaccgtctatcagggcgatggcccactacgtgaaccatcaccctaatcaagttttttggggtcgagg
tgccgtaaagcactaaatcggaaccctaaagggagcccccgatttagagcttgacggggaaagccggcgaacgtggcga
gaaaggaagggaagaaagcgaaaggagcgggcgctagggcgctggcaagtgtagcggtcacgctgcgcgtaaccacc
acacccgccgcgcttaatgcgccgctacagggcgcgtcaggtggcacttttcggggaaatgtgcgcggaaccccctatttgtt
tattttctaaatacattcaaatatgtatccgctcatgagacaataaccctgataaatgcttcaataatattgaaaaaggaagagta
tgagtattcaacatttccgtgtcgcccttattcccttttttgcggcattttgccttcctgtttttgctcacccagaaacgctggtgaaa
gtaaaagatgctgaagatcagttgggtgcacgagtgggttacatcgaactggatctcaacagcggtaagatccttgagagttt
tcgccccgaagaacgttttccaatgatgagcacttttaaagttctgctatgtggcgcggtattatcccgtgttgacgccgggca
agagcaactcggtcgccgcatacactattctcagaatgacttggttgagtactcaccagtcacagaaaagcatcttacggatg
gcatgacagtaagagaattatgcagtgctgccataaccatgagtgataacactgcggccaacttacttctgacaacgatcgg
aggaccgaaggagctaaccgcttttttgcacaacatgggggatcatgtaactcgccttgatcgttgggaaccggagctgaat
gaagccataccaaacgacgagcgtgacaccacgatgcctgcagcaatggcaacaacgttgcgcaaactattaactggcga
actacttactctagcttcccggcaacaattaatagactggatggaggcggataaagttgcaggaccacttctgcgctcggccc
ttccggctggctggtttattgctgataaatctggagccggtgagcgtgggtctcgcggtatcattgcagcactggggccagat
ggtaagccctcccgtatcgtagttatctacacgacggggagtcaggcaactatggatgaacgaaatagacagatcgctgag

Figure 9 Cont.

ataggtgcctcactgattaagcattggtaactgtcagaccaagtttactcatatatactttagattgatttaaaacttcatttttaattt
aaaaggatctaggtgaagatcctttttgataatctcatgaccaaaatcccttaacgtgagttttcgttccactgagcgtcagacc
ccgtagaaaagatcaaaggatcttcttgagatcctttttttctgcgcgtaatctgctgcttgcaaacaaaaaaaccaccgctacc
agcggtggtttgtttgccggatcaagagctaccaactcttttccgaaggtaactggcttcagcagagcgcagataccaaata
ctgtccttctagtgtagccgtagttaggccaccacttcaagaactctgtagcaccgcctacatacctcgctctgctaatcctgtt
accagtggctgctgccagtggcgataagtcgtgtcttaccgggttggactcaagacgatagttaccggataaggcgcagcg
gtcgggctgaacggggggttcgtgcacacagcccagcttggagcgaacgacctacaccgaactgagatacctacagcgt
gagctatgagaaagcgccacgcttcccgaaggggagaaaggcggacaggtatccggtaagcggcagggtcggaacagg
agagcgcacgagggagcttccaggggggaaacgcctggtatctttatagtcctgtcgggtttcgccacctctgacttgagcgt
cgatttttgtgatgctcgtcaggggggcggagcctatggaaaaacgccagcaacgcggccttttacggttcctggccttttg
ctggccttttgctcacatgttctttcctgcgttatcccctgattctgtggataaccgtattaccgcctttgagtgagctgataccgct
cgccgcagccgaacgaccgagcgcagcgagtcagtgagcgaggaagcggaagagcgcctgatgcggtattttctcctta
cgcatctgtgcggtatttcacaccgcaatggtgcactctcagtacaatctgctctgatgccgcatagttaagccagtatacact
ccgctatcgctacgtgactgggtcatggctgcgccccgacacccgccaacacccgctgacgcgccctgacgggcttgtct
gctcccggcatccgcttacagacaagctgtgaccgtctccgggagctgcatgtgtcagaggttttcaccgtcatcaccgaaa
cgcgcgaggcag (SEQ ID NO: 22)

Figure 10

PEX821
gatctcgatcccgcgaaattaatacgactcactatagggagaccacaacggtttccctctagaaataattttgtttaactttaaga
aggagatatacatatgaacgctggtgtcactcagaccccaaaattccaggtcctgaagacaggacagagcatgacactgca
gtgtgcccaggatatgaaccatgaatacatgtcctggtatcgacaagacccaggcatggggctgaggctgattcattactca
gttggtgctggtatcactgaccaaggagaagtccccaatggctacaatgtctccagatcaaccacagaggatttcccgctca
ggctgctgtcggctgctccctcccagacatctgtgtacttctgtgccagcaggccgggactagcgggagggcgaccagag
cagtacttcgggccgggcaccaggctcacggtcacagaggacctgaaaaacgtgttcccacccgaggtcgctgtgtttga
gccatcagaagcagagatctcccacacccaaaaggccacactggtgtgcctggccaccggtttctaccccgaccacgtgg
agctgagctggtgggtgaatgggaaggaggtgcacagtggggtctgcacagacccgcagcccctcaaggagcagcccg
ccctcaatgactccagatacgctctgagcagccgcctgagggtctcggccaccttctggcaggaccccgcaaccacttcc
gctgtcaagtccagttctacgggctctcggagaatgacgagtggacccaggatagggccaaacccgtcacccagatcgtc
agcgccgaggcctggggtagagcagactaagcttgaattccgatccggctgctaacaaagcccgaaaggaagctgagttg
gctgctgccaccgctgagcaataactagcataacccctgggcctctaaacgggtcttgaggggttttttgctgaaaggag
gaactatatccggataattcttgaagacgaaagggcctcgtgatacgcctatttttataggttaatgtcatgataataatggtttct
tagacgtcaggtggcacttttcggggaaatgtgcgcggaaccccatttgtttatttttctaaatacattcaaatatgtatccgctc
atgagacaataaccctgataaatgcttcaataatattttgttaaaattcgcgttaaattttgttaaatcagctcatttttaaccaata
ggccgaaatcggcaaaatcccttataaatcaaaagaatagaccgagatagggttgagtgttgttccagtttggaacaagagt
ccactattaaagaacgtggactccaacgtcaaagggcgaaaaaccgtctatcagggcgatggcccactacgtgaaccatca
ccctaatcaagttttttggggtcgaggtgccgtaaagcactaaatcggaaccctaaagggagcccccgatttagagcttgac
ggggaaagccggcgaacgtggcgagaaaggaagggaagaaagcgaaaggagcgggcgctagggcgctggcaagtg
tagcggtcacgctgcgcgtaaccaccacacccgccgcgcttaatgcgccgctacagggcgcgtcaggtggcacttttcgg
ggaaatgtgcgcggaaccccatttgtttatttttctaaatacattcaaatatgtatccgctcatgagacaataaccctgataaatg
cttcaataatattgaaaaaggaagagtatgagtattcaacatttccgtgtcgcccttattcccttttttgcggcattttgccttcctgt
ttttgctcacccagaaacgctggtgaaagtaaaagatgctgaagatcagttgggtgcacgagtgggttacatcgaactggat
ctcaacagcggtaagatccttgagagttttcgccccgaagaacgttttccaatgatgagcacttttaaagttctgctatgtggcg
cggtattatcccgtgttgacgccgggcaagagcaactcggtcgccgcatacactattctcagaatgacttggttgagtactca
ccagtcacagaaaagcatcttacggatggcatgacagtaagagaattatgcagtgctgccataaccatgagtgataacactg
cggccaacttacttctgacaacgatcggaggaccgaaggagctaaccgcttttttgcacaacatgggggatcatgtaactcg
ccttgatcgttgggaaccggagctgaatgaagccataccaaacgacgagcgtgacaccacgatgcctgcagcaatggcaa
caacgttgcgcaaactattaactggcgaactacttactctagcttcccggcaacaattaatagactggatggaggcggataaa
gttgcaggaccacttctgcgctcggcccttccggctggctggtttattgctgataaatctggagccggtgagcgtgggtctcg
cggtatcattgcagcactggggccagatggtaagccctcccgtatcgtagttatctacacgacggggagtcaggcaactatg
gatgaacgaaatagacagatcgctgagataggtgcctcactgattaagcattggtaactgtcagaccaagtttactcatatata
ctttagattgatttaaaacttcattttttaatttaaaaggatctaggtgaagatcctttttgataatctcatgaccaaaatcccttaacgt
gagttttcgttccactgagcgtcagaccccgtagaaaagatcaaaggatcttcttgagatccttttttctgcgcgtaatctgctg
cttgcaaacaaaaaaaccaccgctaccagcggtggtttgtttgccggatcaagagctaccaactctttttccgaaggtaactg
gcttcagcagagcgcagataccaaatactgtccttctagtgtagccgtagttaggccaccacttcaagaactctgtagcaccg
cctacatacctcgctctgctaatcctgttaccagtggctgctgccagtggcgataagtcgtgtcttaccgggttggactcaaga
cgatagttaccggataaggcgcagcggtcgggctgaacggggggttcgtgcacacagcccagcttggagcgaacgacct
acaccgaactgagatacctacagcgtgagctatgagaaagcgccacgcttcccgaagggagaaaggcggacaggtatcc

Figure 10 Cont.

ggtaagcggcagggtcggaacaggagagcgcacgagggagcttccaggggggaaacgcctggtatctttatagtcctgtc
gggtttcgccacctctgacttgagcgtcgattttgtgatgctcgtcagggggggcggagcctatggaaaaacgccagcaacg
cggccttttacggttcctggccttttgctggccttttgctcacatgttctttcctgcgttatcccctgattctgtggataaccgtatta
ccgcctttgagtgagctgataccgctcgccgcagccgaacgaccgagcgcagcgagtcagtgagcgaggaagcggaag
agcgcctgatgcggtattttctccttacgcatctgtgcggtatttcacaccgcaatggtgcactctcagtacaatctgctctgatg
ccgcatagttaagccagtatacactccgctatcgctacgtgactgggtcatggctgcgccccgacacccgccaacacccgc
tgacgcgccctgacgggcttgtctgctcccggcatccgcttacagacaagctgtgaccgtctccgggagctgcatgtgtcag
aggttttcaccgtcatcaccgaaacgcgcgaggcag
(SEQ ID NO: 23)

Figure 11

```
M E A G V T Q S P T H L I K T R G Q Q V T L R C S P K S G H D T V S W
Y Q Q A L G Q G P Q F I F Q Y Y E E E E R Q R G N F P D R F S G H Q F
P N Y S S E L N V N A L L L G D S A L Y L C A S S D T V S Y E Q Y F G
P G T R L T V T E D L K N V F P P E V A V F E P S E A E I S H T Q K A
T L V C L A T G F Y P D H V E L S W W V N G K E V H S G V C T D P Q P
L K E Q P A L N D S R Y A L S S R L R V S A T F W Q D P R N H F R C Q
V Q F Y G L S E N D E W T Q D R A K P V T Q I V S A E A W G R A D P G
A P T S S S T K K T Q L Q L E H L L L D L Q M I L N G I N N Y K N P K
L T R M L T F K F Y M P K K A T E L K H L Q C L E E E L K P L E E V L
N L A Q S K N F H L R P R D L I S N I N V I V L E L K G S E T T F M C
E Y A D E T A T I V E F L N R W I T F C Q S I I S T L T
```
(SEQ ID NO: 24)

Figure 12
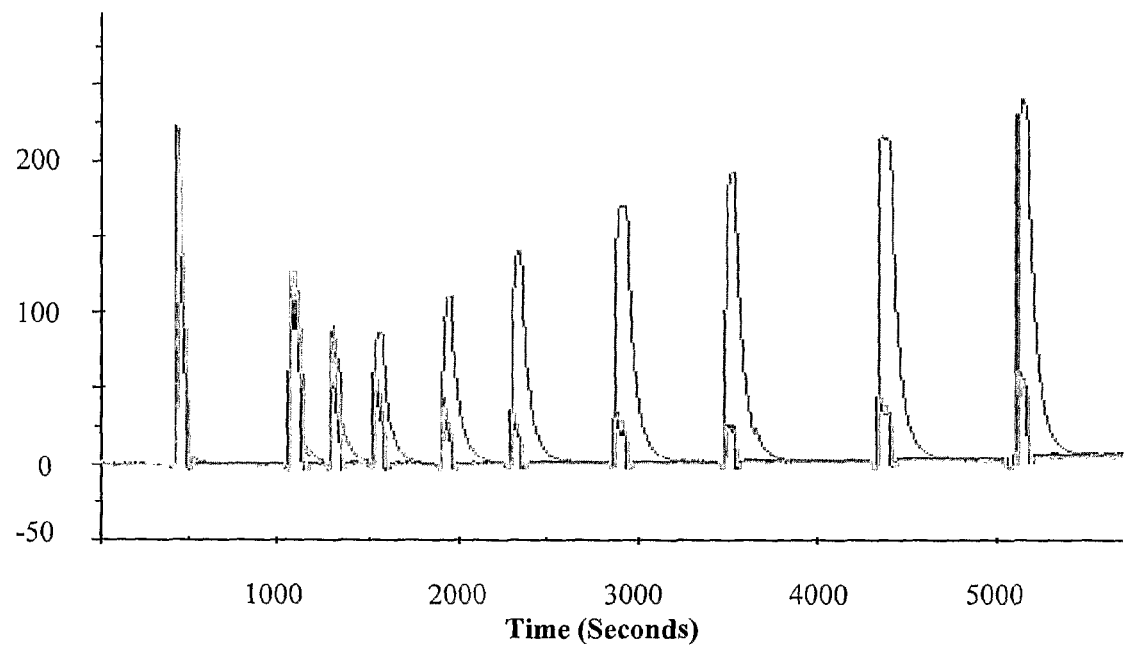
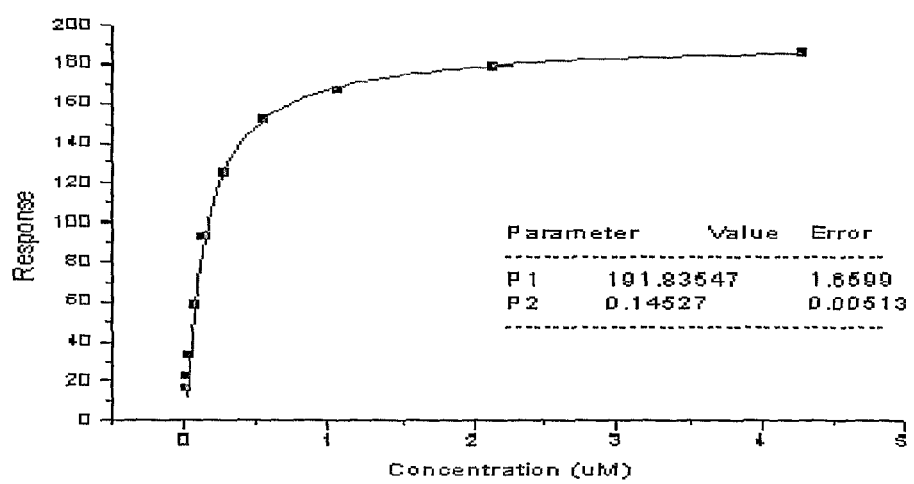

Figure 15a atgatgaagagcctgagggtgctgctggtgatcctgtggctgcagctgtcctgggtgtggagccagcag
aaggaggtggagcagaatagcggccctctgagcgtgcccgagggcgccatcgccagcctgaactgtacc
tacagcgacagaggcagccagagcttcttctggtacaggcagtacagcggcaagagccccgagctgatt
atgttcatctacagcaacggcgacaaggaggacggcagattcaccgcccagctgaacaaggccagccag
tacatcagcctgctgatccgggatagcaagctgtccgacagcgccacctacctgtgtgccgtgagaacc
aatagcggctacgccctgaatttcggcaagggcaccagcctgctggtgaccccccacatccagaatcct
gaccccgccgtgtaccagctgagagacagcaagagcagcgacaagagcgtgtgtctgttcaccgacttc
gacagccagaccaacgtgtcccagagcaaggacagcgacgtgtacatcaccgacaagaccgtgctggac
atgaggagcatggacttcaagagcaacagcgccgtggcctggagcaacaagagcgacttcgcctgtgcc
aacgccttcaacaacagcatcatccccgaggacaccttttccccagccctgagagcagctgtgacgtg
aaactggtggagaagagcttcgagaccgacaccaacctgaacttccagaacctgagcgtgatcggcttc
agaatcctgctgctgaaggtggccggattcaacctgctgatgaccctgagactgtggagcagc
(SEQ ID NO: 25)

Figure 15b atgggacccggcctgctgtgctgggccctgctgtgcctgctgggagccggactggtggacgccggagtg
acccagagccccaccacctgattaagaccaggggccagcaggtgaccctgagatgtagccctaagagc
ggccacgataccgtgtcctggtatcagcaggccctgggccagggaccccagttcatcttccagtactac
gaggaggaggagaggcagagaggcaacttccccgacagattcagcggccaccagttccccaattacagc
agcgagctgaacgtgaatgccctgctgctgggcgacagcgccctgtacctgtgtgccagcagcgacaca
gtgagctacgagcagtacttcggccctggcaccagactgaccgtgaccgaggacctgaagaacgtgttc
cctcctgaggtggccgtgttcgagccagcgaggccgagatcagccacacccagaaggccaccctggtg
tgtctggccaccggcttctaccccgaccacgtggagctgtcctggtgggtgaacggcaaggaggtgcac
agcggcgtgtccaccgaccccagcccctgaaggagcagccgccctgaacgatagcaggtactgcctg
agcagcaggctgagagtgagcgccaccttctggcagaaccccggaaccacttcagatgccaggtgcag
ttctacggcctgagcgagaacgacgagtggacccaggatagagccaagcccgtgacccagatcgtgtcc
gccgaggcctgggcagagccgactgtggcttcaccagcgagagctaccagcagggcgtgctgtccgcc
accatcctgtacgagatcctgctgggcaaggccacactgtacgccgtgctggtgtccgccctggtgctg
atggctatggtgaagcggaaggacagcaggggc
(SEQ ID NO: 26)

Figure 16a

```
M M K S L R V L L V I L W L Q L S W V W S Q Q K E V E Q N S G P L S V
P E G A I A S L N C T Y S D R G S Q S F F W Y R Q Y S G K S P E L I M
F I Y S N G D K E D G R F T A Q L N K A S Q Y I S L L I R D S K L S D
S A T Y L C A V R T N S G Y A L N F G K G T S L L V T P H I Q N P D P
A V Y Q L R D S K S S D K S V C L F T D F D S Q T N V S Q S K D S D V
Y I T D K T V L D M R S M D F K S N S A V A W S N K S D F A C A N A F
N N S I I P E D T F F P S P E S S C D V K L V E K S F E T D T N L N F
Q N L S V I G F R I L L L K V A G F N L L M T L R L W S S
```
(SEQ ID NO: 27)

Figure 16b

```
M G P G L L C W A L L C L L G A G L V D A G V T Q S P T H L I K T R G
Q Q V T L R C S P K S G H D T V S W Y Q Q A L G Q G P Q F I F Q Y Y E
E E E R Q R G N F P D R F S G H Q F P N Y S S E L N V A L L L G D S
A L Y L C A S S D T V S Y E Q Y F G P G T R L T V T E D L K N V F P P
E V A V F E P S E A E I S H T Q K A T L V C L A T G F Y P D H V E L S
W W V N G K E V H S G V S T D P Q P L K E Q P A L N D S R Y C L S S R
L R V S A T F W Q N P R N H F R C Q V Q F Y G L S E N D E W T Q D R A
K P V T Q I V S A E A W G R A D C G F T S E S Y Q Q G V L S A T I L Y
E I L L G K A T L Y A V L V S A L V L M A M V K R K D S R G
```
(SEQ ID NO: 28)

Figure 18a

M A Q K E V E Q N S G P L S V P E G A I A S L N C T Y S D R
G S Q S F F W Y R Q Y S G K S P E L I M F I Y S N G D K E D
G R F T A Q L N K A S Q Y I S L L I R D S K L S D S A T Y L
C A V R G A H D Y A L N F G K G T S L L V T P H I Q N P D P
A V Y Q L R D S K S S D K S V C L F T D F D S Q T N V S Q S
K D S D V Y I T D K C V L D M R S M D F K S N S A V A W S N
K S D F A C A N A F N N S I I P E D T F F P S P E S S
(SEQ ID NO: 29)

Figure 18b

M E A G V T Q S P T H L I K T R G Q Q V T L R C S P K S G H
D T V S W Y Q Q A L G Q G P Q F I F Q Y A L G E E R Q R G N
F P D R F S G H Q F P N Y S S E L N V A L L L G D S A L Y
L C A S S D T V S Y E Q Y F G P G T R L T V T E D L K N V F
P P E V A V F E P S E A E I S H T Q K A T L V C L A T G F Y
P D H V E L S W W V N G K E V H S G V C T D P Q P L K E Q P
A L N D S R Y A L S S R L R V S A T F W Q D P R N H F R C Q
V Q F Y G L S E N D E W T Q D R A K P V T Q I V S A E A W G
R A D
(SEQ ID NO: 30)

SEQUENCE LISTING

<160> NUMBER OF SEQ ID NOS: 31

<210> SEQ ID NO 1
<211> LENGTH: 114
<212> TYPE: PRT
<213> ORGANISM: Homo sapiens

<400> SEQUENCE: 1

Met Ala Gln Lys Glu Val Glu Gln Asn Ser Gly Pro Leu Ser Val Pro
1               5                   10                  15

Glu Gly Ala Ile Ala Ser Leu Asn Cys Thr Tyr Ser Asp Arg Gly Ser
            20                  25                  30

Gln Ser Phe Phe Trp Tyr Arg Gln Tyr Ser Gly Lys Ser Pro Glu Leu
        35                  40                  45

Ile Met Phe Ile Tyr Ser Asn Gly Asp Lys Glu Asp Gly Arg Phe Thr
    50                  55                  60

Ala Gln Leu Asn Lys Ala Ser Gln Tyr Ile Ser Leu Leu Ile Arg Asp
65                  70                  75                  80

Ser Lys Leu Ser Asp Ser Ala Thr Tyr Leu Cys Ala Val Arg Thr Asn
                85                  90                  95

Ser Gly Tyr Ala Leu Asn Phe Gly Lys Gly Thr Ser Leu Leu Val Thr
            100                 105                 110

Pro His

<210> SEQ ID NO 2
<211> LENGTH: 113
<212> TYPE: PRT
<213> ORGANISM: Homo sapiens

<400> SEQUENCE: 2

Met Glu Ala Gly Val Thr Gln Ser Pro Thr His Leu Ile Lys Thr Arg
1               5                   10                  15

Gly Gln Gln Val Thr Leu Arg Cys Ser Pro Lys Ser Gly His Asp Thr
            20                  25                  30

Val Ser Trp Tyr Gln Gln Ala Leu Gly Gln Gly Pro Gln Phe Ile Phe
        35                  40                  45

Gln Tyr Tyr Glu Glu Glu Glu Arg Gln Arg Gly Asn Phe Pro Asp Arg
    50                  55                  60

Phe Ser Gly His Gln Phe Pro Asn Tyr Ser Ser Glu Leu Asn Val Asn
65                  70                  75                  80

Ala Leu Leu Leu Gly Asp Ser Ala Leu Tyr Leu Cys Ala Ser Ser Asp
                85                  90                  95

Thr Val Ser Tyr Glu Gln Tyr Phe Gly Pro Gly Thr Arg Leu Thr Val
            100                 105                 110

Thr

<210> SEQ ID NO 3
<211> LENGTH: 624
<212> TYPE: DNA
<213> ORGANISM: Artificial Sequence
<220> FEATURE:
<223> OTHER INFORMATION: DNA encoding a truncated portion of the
      parental GAG TCR alpha chain

<400> SEQUENCE: 3
atggcccaga aggaggtgga gcagaattct ggacccctca gtgttccaga gggagccatt      60
gcctctctca attgcactta cagtgaccga ggttcccagt ccttcttctg gtacagacaa     120

```
tattctggga aaagccctga gttgataatg ttcatatact ccaatggtga caaagaagat    180
ggaaggttta cagcacagct caataaagcc agccagtata tttccctgct catcagagac    240
tccaagctca gtgattcagc cacctacctc tgtgcggtgc gcacaaattc cgggtatgca    300
ctcaacttcg gcaaaggcac ctcgctgttg gtcacacccc atatccagaa ccctgaccct    360
gccgtgtacc agctgagaga ctctaaatcc agtgacaagt ctgtctgcct attcaccgat    420
tttgattctc aaacaaatgt gtcacaaagt aaggattctg atgtgtatat cacagacaaa    480
actgtgctag acatgaggtc tatggacttc aagagcaaca gtgctgtggc ctggagcaac    540
aaatctgact ttgcatgtgc aaacgccttc aacaacagca ttattccaga agacaccttc    600
ttccccagcc agaaagttc ctaa    624

<210> SEQ ID NO 4
<211> LENGTH: 732
<212> TYPE: DNA
<213> ORGANISM: Artificial Sequence
<220> FEATURE:
<223> OTHER INFORMATION: dna encoding a truncated portion of the
      parental gag tcr beta chain

<400> SEQUENCE: 4
atggaggctg gagtcacaca aagtcccaca cacctgatca aaacgagagg acagcaagtg     60
actctgagat gctctcctaa gtctgggcat gacactgtgt cctggtacca acaggccctg    120 ggtcagggc cccagtttat ctttcagtat tatgaggagg aagagagaca gagaggcaac    180
ttccctgatc gattctcagg tcaccagttc cctaactata gctctgagct gaatgtgaac    240
gccttgttgc tgggggactc ggccctctat ctctgtgcca gcagcgacac cgtctcctac    300
gagcagtact tcgggccggg caccaggctc acggtcacag gacctgaaa aacgtgttc    360 ccacccgagg tcgctgtgtt tgagccatca gaagcagaga tctcccacac ccaaaaggcc    420
acactggtgt gcctggccac aggcttctac cccgaccacg tggagctgag ctggtgggtg    480
aatgggaagg aggtgcacag tggggtcagc acagacccgc agcccctcaa ggagcagccc    540
gccctcaatg actccagata cgctctgagc agccgcctga gggtctcggc cacctctctgg    600 caggaccccc gcaaccactt ccgctgtcaa gtccagttct acgggctctc ggagaatgac    660
gagtggaccc aggataggc caaacccgtc acccagatcg tcagcgccga ggcctggggt    720
agagcagact aa    732

<210> SEQ ID NO 5
<211> LENGTH: 207
<212> TYPE: PRT
<213> ORGANISM: Artificial Sequence
<220> FEATURE:
<223> OTHER INFORMATION: a truncated portion of the parental gag tcr
      alpha chain

<400> SEQUENCE: 5

Met Ala Gln Lys Glu Val Glu Gln Asn Ser Gly Pro Leu Ser Val Pro
1               5                   10                  15

Glu Gly Ala Ile Ala Ser Leu Asn Cys Thr Tyr Ser Asp Arg Gly Ser
            20                  25                  30

Gln Ser Phe Phe Trp Tyr Arg Gln Tyr Ser Gly Lys Ser Pro Glu Leu
        35                  40                  45

Ile Met Phe Ile Tyr Ser Asn Gly Asp Lys Glu Asp Gly Arg Phe Thr
    50                  55                  60

Ala Gln Leu Asn Lys Ala Ser Gln Tyr Ile Ser Leu Leu Ile Arg Asp
```

```
                65                  70                  75                  80
Ser Lys Leu Ser Asp Ser Ala Thr Tyr Leu Cys Ala Val Arg Thr Asn
                    85                  90                  95
Ser Gly Tyr Ala Leu Asn Phe Gly Lys Gly Thr Ser Leu Leu Val Thr
                   100                 105                 110
Pro His Ile Gln Asn Pro Asp Pro Ala Val Tyr Gln Leu Arg Asp Ser
                   115                 120                 125
Lys Ser Ser Asp Lys Ser Val Cys Leu Phe Thr Asp Phe Asp Ser Gln
                   130                 135                 140
Thr Asn Val Ser Gln Ser Lys Asp Ser Asp Val Tyr Ile Thr Asp Lys
145                 150                 155                 160
Thr Val Leu Asp Met Arg Ser Met Asp Phe Lys Ser Asn Ser Ala Val
                   165                 170                 175
Ala Trp Ser Asn Lys Ser Asp Phe Ala Cys Ala Asn Ala Phe Asn Asn
                   180                 185                 190
Ser Ile Ile Pro Glu Asp Thr Phe Phe Pro Ser Pro Glu Ser Ser
                   195                 200                 205

<210> SEQ ID NO 6
<211> LENGTH: 243
<212> TYPE: PRT
<213> ORGANISM: Artificial Sequence
<220> FEATURE:
<223> OTHER INFORMATION: a truncated portion of the parental gag tcr
      beta chain

<400> SEQUENCE: 6

Met Glu Ala Gly Val Thr Gln Ser Pro Thr His Leu Ile Lys Thr Arg
1               5                   10                  15
Gly Gln Gln Val Thr Leu Arg Cys Ser Pro Lys Ser Gly His Asp Thr
                20                  25                  30
Val Ser Trp Tyr Gln Gln Ala Leu Gly Gln Gly Pro Gln Phe Ile Phe
                35                  40                  45
Gln Tyr Tyr Glu Glu Glu Glu Arg Gln Arg Gly Asn Phe Pro Asp Arg
            50                  55                  60
Phe Ser Gly His Gln Phe Pro Asn Tyr Ser Ser Glu Leu Asn Val Asn
65                  70                  75                  80
Ala Leu Leu Leu Gly Asp Ser Ala Leu Tyr Leu Cys Ala Ser Ser Asp
                85                  90                  95
Thr Val Ser Tyr Glu Gln Tyr Phe Gly Pro Gly Thr Arg Leu Thr Val
                   100                 105                 110
Thr Glu Asp Leu Lys Asn Val Phe Pro Pro Glu Val Ala Val Phe Glu
                   115                 120                 125
Pro Ser Glu Ala Glu Ile Ser His Thr Gln Lys Ala Thr Leu Val Cys
                   130                 135                 140
Leu Ala Thr Gly Phe Tyr Pro Asp His Val Glu Leu Ser Trp Trp Val
145                 150                 155                 160
Asn Gly Lys Glu Val His Ser Gly Val Ser Thr Asp Pro Gln Pro Leu
                   165                 170                 175
Lys Glu Gln Pro Ala Leu Asn Asp Ser Arg Tyr Ala Leu Ser Ser Arg
                   180                 185                 190
Leu Arg Val Ser Ala Thr Phe Trp Gln Asp Pro Arg Asn His Phe Arg
                   195                 200                 205
Cys Gln Val Gln Phe Tyr Gly Leu Ser Glu Asn Asp Glu Trp Thr Gln
                   210                 215                 220
Asp Arg Ala Lys Pro Val Thr Gln Ile Val Ser Ala Glu Ala Trp Gly
```

Arg Ala Asp

<210> SEQ ID NO 7
<211> LENGTH: 630
<212> TYPE: DNA
<213> ORGANISM: Artificial Sequence
<220> FEATURE:
<223> OTHER INFORMATION: DNA encoding a truncated portion of the
      parental gag tcr alpha chain including an introduced Cys codon
      and restriction enzyme recognition sequences

<400> SEQUENCE: 7

```
ccatcgatgg cccagaagga ggtggagcag aattctggac ccctcagtgt tccagaggga      60
gccattgcct ctctcaattg cacttacagt gaccgaggtt cccagtcctt cttctggtac     120
agacaatatt ctgggaaaag ccctgagttg ataatgttca tatactccaa tggtgacaaa     180
gaagatggaa ggtttacagc acagctcaat aaagccagcc agtatatttc cctgctcatc     240
agagactcca agctcagtga ttcagccacc tacctctgtg cggtgcgcac aaattccggg     300
tatgcactca acttcggcaa aggcaccctg ctgttggtca cccccatat ccagaaccct      360
gaccctgccg tgtaccagct gagagactct aagtcgagtg acaagtctgt ctgcctattc     420
accgattttg attctcaaac aaatgtgtca caaagtaagg attctgatgt gtatatcaca     480
gacaaatgtg tgctagacat gaggtctatg gacttcaaga gcaacagtgc tgtggcctgg     540
agcaacaaat ctgactttgc atgtgcaaac gccttcaaca cagcattat tccagaagac      600
accttcttcc ccagcccaga aagttcctaa                                      630
```

<210> SEQ ID NO 8
<211> LENGTH: 742
<212> TYPE: DNA
<213> ORGANISM: Artificial Sequence
<220> FEATURE:
<223> OTHER INFORMATION: DNA encoding a truncated portion of the
      parental gag tcr beta chain including an introduced Cys codon
      and restriction enzyme recognition sequences

<400> SEQUENCE: 8

```
tctctcatta atggaggctg gagtcacaca aagtcccaca cacctgatca aaacgagagg      60
acagcaagtg actctgagat gctctcctaa gtctgggcat gacactgtgt cctggtacca     120
acaggccctg ggtcaggggc ccagtttat cttttcagtat tatgaggagg aagagagaca     180
gagaggcaac ttccctgatc gattctcagg tcaccagttc cctaactata gctctgagct     240
gaatgtgaac gccttgttgc tgggggactc ggccctctat ctctgtgcca gcagcgacac     300
cgtctcctac gagcagtact tcgggccggg caccaggctc acggtcacag aggacctgaa     360
aaacgtgttc ccacccgagg tcgctgtgtt tgagccatca gaagcagaga tctcccacac     420
ccaaaaggcc acactggtgt gcctggccac cggtttctac cccgaccacg tggagctgag     480
ctggtgggtg aatgggaagg aggtgcacag tggggtctgc acagaccgc agcccctcaa      540
ggagcagccc gccctcaatg actccagata cgctctgagc agccgcctga ggtctcggc     600
caccttctgg caggaccccc gcaaccactt ccgctgtcaa gtccagttct acgggctctc     660
ggagaatgac gagtggaccc aggatagggc caaacccgtc acccagatcg tcagcgccga     720
ggcctggggt agagcagact aa                                              742
```

<210> SEQ ID NO 9
<211> LENGTH: 207
<212> TYPE: PRT

```
<213> ORGANISM: Artificial Sequence
<220> FEATURE:
<223> OTHER INFORMATION: A truncated portion of the parental gag tcr
      alpha chain including an introduced Cys residue

<400> SEQUENCE: 9

Met Ala Gln Lys Glu Val Glu Gln Asn Ser Gly Pro Leu Ser Val Pro
1               5                   10                  15

Glu Gly Ala Ile Ala Ser Leu Asn Cys Thr Tyr Ser Asp Arg Gly Ser
            20                  25                  30

Gln Ser Phe Phe Trp Tyr Arg Gln Tyr Ser Gly Lys Ser Pro Glu Leu
        35                  40                  45

Ile Met Phe Ile Tyr Ser Asn Gly Asp Lys Glu Asp Gly Arg Phe Thr
    50                  55                  60

Ala Gln Leu Asn Lys Ala Ser Gln Tyr Ile Ser Leu Leu Ile Arg Asp
65                  70                  75                  80

Ser Lys Leu Ser Asp Ser Ala Thr Tyr Leu Cys Ala Val Arg Thr Asn
                85                  90                  95

Ser Gly Tyr Ala Leu Asn Phe Gly Lys Gly Thr Ser Leu Leu Val Thr
            100                 105                 110

Pro His Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
    130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser
        195                 200                 205

<210> SEQ ID NO 10
<211> LENGTH: 243
<212> TYPE: PRT
<213> ORGANISM: Artificial Sequence
<220> FEATURE:
<223> OTHER INFORMATION: A truncated portion of the parental gag tcr
      beta chain including an introduced Cys

<400> SEQUENCE: 10

Met Glu Ala Gly Val Thr Gln Ser Pro Thr His Leu Ile Lys Thr Arg
1               5                   10                  15

Gly Gln Gln Val Thr Leu Arg Cys Ser Pro Lys Ser Gly His Asp Thr
            20                  25                  30

Val Ser Trp Tyr Gln Gln Ala Leu Gly Gln Gly Pro Gln Phe Ile Phe
        35                  40                  45

Gln Tyr Tyr Glu Glu Glu Arg Gln Arg Gly Asn Phe Pro Asp Arg
    50                  55                  60

Phe Ser Gly His Gln Phe Pro Asn Tyr Ser Ser Glu Leu Asn Val Asn
65                  70                  75                  80

Ala Leu Leu Leu Gly Asp Ser Ala Leu Tyr Leu Cys Ala Ser Ser Asp
                85                  90                  95

Thr Val Ser Tyr Glu Gln Tyr Phe Gly Pro Gly Thr Arg Leu Thr Val
            100                 105                 110

Thr Glu Asp Leu Lys Asn Val Phe Pro Pro Glu Val Ala Val Phe Glu
        115                 120                 125
```

```
Pro Ser Glu Ala Glu Ile Ser His Thr Gln Lys Ala Thr Leu Val Cys
        130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
                180                 185                 190

Leu Arg Val Ser Ala Thr Phe Trp Gln Asp Pro Arg Asn His Phe Arg
            195                 200                 205

Cys Gln Val Gln Phe Tyr Gly Leu Ser Glu Asn Asp Glu Trp Thr Gln
210                 215                 220

Asp Arg Ala Lys Pro Val Thr Gln Ile Val Ser Ala Glu Ala Trp Gly
225                 230                 235                 240

Arg Ala Asp

<210> SEQ ID NO 11
<211> LENGTH: 114
<212> TYPE: PRT
<213> ORGANISM: Artificial Sequence
<220> FEATURE:
<223> OTHER INFORMATION: High affinity mutated GAG TCR alpha chain
      variable region sequence

<400> SEQUENCE: 11

Met Ala Gln Lys Glu Val Glu Gln Asn Ser Gly Pro Leu Ser Val Pro
1               5                   10                  15

Glu Gly Ala Ile Ala Ser Leu Asn Cys Thr Tyr Ser Asp Arg Gly Ser
                20                  25                  30

Gln Ser Phe Phe Trp Tyr Arg Gln Tyr Ser Gly Lys Ser Pro Glu Leu
            35                  40                  45

Ile Met Phe Ile Tyr Ser Asn Gly Asp Lys Glu Asp Gly Arg Phe Thr
        50                  55                  60

Ala Gln Leu Asn Lys Ala Ser Gln Tyr Ile Ser Leu Leu Ile Arg Asp
65                  70                  75                  80

Ser Lys Leu Ser Asp Ser Ala Thr Tyr Leu Cys Ala Val Arg Ser Ala
                85                  90                  95

His Gly Tyr Ser Leu Asn Phe Gly Lys Gly Thr Ser Leu Leu Val Thr
                100                 105                 110

Pro His

<210> SEQ ID NO 12
<211> LENGTH: 114
<212> TYPE: PRT
<213> ORGANISM: Artificial Sequence
<220> FEATURE:
<223> OTHER INFORMATION: High affinity mutated GAG TCR alpha chain
      variable region sequence

<400> SEQUENCE: 12

Met Ala Gln Lys Glu Val Glu Gln Asn Ser Gly Pro Leu Ser Val Pro
1               5                   10                  15

Glu Gly Ala Ile Ala Ser Leu Asn Cys Thr Tyr Ser Asp Arg Gly Ser
                20                  25                  30

Gln Ser Phe Phe Trp Tyr Arg Gln Tyr Ser Gly Lys Ser Pro Glu Leu
            35                  40                  45

Ile Met Phe Ile Tyr Ser Asn Gly Asp Lys Glu Asp Gly Arg Phe Thr
        50                  55                  60
```

```
Ala Gln Leu Asn Lys Ala Ser Gln Tyr Ile Ser Leu Ile Arg Asp
 65                  70                  75                  80

Ser Lys Leu Ser Asp Ser Ala Thr Tyr Leu Cys Ala Val Arg Ser Ala
                 85                  90                  95

His Gly Tyr Ala Leu Asn Phe Gly Lys Gly Thr Ser Leu Leu Val Thr
            100                 105                 110

Pro His

<210> SEQ ID NO 13
<211> LENGTH: 114
<212> TYPE: PRT
<213> ORGANISM: Artificial Sequence
<220> FEATURE:
<223> OTHER INFORMATION: High affinity mutated GAG TCR alpha chain
      variable region sequence

<400> SEQUENCE: 13

Met Ala Gln Lys Glu Val Glu Gln Asn Ser Gly Pro Leu Ser Val Pro
  1               5                  10                  15

Glu Gly Ala Ile Ala Ser Leu Asn Cys Thr Tyr Ser Asp Arg Gly Ser
                 20                  25                  30

Gln Ser Phe Phe Trp Tyr Arg Gln Tyr Ser Gly Lys Ser Pro Glu Leu
             35                  40                  45

Ile Met Phe Ile Tyr Ser Asn Gly Asp Lys Glu Asp Gly Arg Phe Thr
 50                  55                  60

Ala Gln Leu Asn Lys Ala Ser Gln Tyr Ile Ser Leu Leu Ile Arg Asp
 65                  70                  75                  80

Ser Lys Leu Ser Asp Ser Ala Thr Tyr Leu Cys Ala Val Arg Gly Ala
                 85                  90                  95

His Asp Tyr Ala Leu Asn Phe Gly Lys Gly Thr Ser Leu Leu Val Thr
            100                 105                 110

Pro His

<210> SEQ ID NO 14
<211> LENGTH: 113
<212> TYPE: PRT
<213> ORGANISM: Artificial Sequence
<220> FEATURE:
<223> OTHER INFORMATION: High affinity mutated GAG TCR beta chain
      variable region sequence

<400> SEQUENCE: 14

Met Glu Ala Gly Val Thr Gln Ser Pro Thr His Leu Ile Lys Thr Arg
  1               5                  10                  15

Gly Gln Gln Val Thr Leu Arg Cys Ser Pro Lys Ser Gly His Asp Thr
                 20                  25                  30

Val Ser Trp Tyr Gln Gln Ala Leu Gly Gln Gly Pro Gln Phe Ile Phe
             35                  40                  45

Gln Tyr Val Arg Gly Val Glu Arg Gln Arg Gly Asn Phe Pro Asp Arg
 50                  55                  60

Phe Ser Gly His Gln Phe Pro Asn Tyr Ser Ser Glu Leu Asn Val Asn
 65                  70                  75                  80

Ala Leu Leu Leu Gly Asp Ser Ala Leu Tyr Leu Cys Ala Ser Ser Asp
                 85                  90                  95

Thr Val Ser Tyr Glu Gln Tyr Phe Gly Pro Gly Thr Arg Leu Thr Val
            100                 105                 110

Thr
```

```
<210> SEQ ID NO 15
<211> LENGTH: 113
<212> TYPE: PRT
<213> ORGANISM: Artificial Sequence
<220> FEATURE:
<223> OTHER INFORMATION: High affinity mutated GAG TCR beta chain
      variable region sequence

<400> SEQUENCE: 15

Met Glu Ala Gly Val Thr Gln Ser Pro Thr His Leu Ile Lys Thr Arg
1               5                   10                  15

Gly Gln Gln Val Thr Leu Arg Cys Ser Pro Lys Ser Gly His Asp Thr
            20                  25                  30

Val Ser Trp Tyr Gln Gln Ala Leu Gly Gln Gly Pro Gln Phe Ile Phe
        35                  40                  45

Gln Tyr Ala Leu Gly Glu Glu Arg Gln Arg Gly Asn Phe Pro Asp Arg
    50                  55                  60

Phe Ser Gly His Gln Phe Pro Asn Tyr Ser Glu Leu Asn Val Asn
65                  70                  75                  80

Ala Leu Leu Leu Gly Asp Ser Ala Leu Tyr Leu Cys Ala Ser Ser Asp
                85                  90                  95

Thr Val Ser Tyr Glu Gln Tyr Phe Gly Pro Gly Thr Arg Leu Thr Val
            100                 105                 110

Thr

<210> SEQ ID NO 16
<211> LENGTH: 9
<212> TYPE: PRT
<213> ORGANISM: Human immunodeficiency virus

<400> SEQUENCE: 16

Ser Leu Tyr Asn Thr Val Ala Thr Leu
1               5

<210> SEQ ID NO 17
<211> LENGTH: 30
<212> TYPE: PRT
<213> ORGANISM: Artificial Sequence
<220> FEATURE:
<223> OTHER INFORMATION: Short scTCR linker

<400> SEQUENCE: 17

Pro Gly Gly Gly Ser Gly Gly Gly Ser Gly Gly Gly Ser Gly
1               5                   10                  15

Gly Gly Gly Ser Gly Gly Gly Gly Ser Gly Gly Gly Gly Pro
            20                  25                  30

<210> SEQ ID NO 18
<211> LENGTH: 35
<212> TYPE: PRT
<213> ORGANISM: Artificial Sequence
<220> FEATURE:
<223> OTHER INFORMATION: Long scTCR linker

<400> SEQUENCE: 18

Pro Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Pro
        35
```

<210> SEQ ID NO 19
<211> LENGTH: 46
<212> TYPE: PRT
<213> ORGANISM: Artificial Sequence
<220> FEATURE:
<223> OTHER INFORMATION: Truncated portion of the amino acid sequence
      encoded by TRAC

<400> SEQUENCE: 19

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys
        35                  40                  45

<210> SEQ ID NO 20
<211> LENGTH: 56
<212> TYPE: PRT
<213> ORGANISM: Artificial Sequence
<220> FEATURE:
<223> OTHER INFORMATION: Truncated portion of the amino acid sequence
      encoded by TRBC1

<400> SEQUENCE: 20

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val
    50                  55

<210> SEQ ID NO 21
<211> LENGTH: 56
<212> TYPE: PRT
<213> ORGANISM: Artificial Sequence
<220> FEATURE:
<223> OTHER INFORMATION: Truncated portion of the amino acid sequence
      encoded by TRBC2

<400> SEQUENCE: 21

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val
    50                  55

<210> SEQ ID NO 22
<211> LENGTH: 3342
<212> TYPE: DNA
<213> ORGANISM: Artificial Sequence
<220> FEATURE:
<223> OTHER INFORMATION: pEX954 vector

<400> SEQUENCE: 22
gatctcgatc ccgcgaaatt aatacgactc actataggga gaccacaacg gtttccctct     60
agaaataatt ttgtttaact ttaagaagga gatataatcg atgtctaact cgagtgacaa    120

```
gtctgtctgc ctattcaccg attttgattc tcaaacaaat gtgtcacaaa gtaaggattc    180
tgatgtgtat atcacagaca aatgtgtgct agacatgagg tctatggact tcaagagcaa    240
cagtgctgtg gcctggagca acaaatctga cttgtcatgt gcaaacgcct tcaacaacag    300
cattattcca gaagacacct tcttccccag cccagaaagt tcctaagctt gaattccgat    360
ccggctgcta acaaagcccg aaaggaagct gagttggctg ctgccaccgc tgagcaataa    420
ctagcataac cccttggggc tctaaacgg gtcttgaggg gttttttgct gaaaggagga    480
actatatccg gataattctt gaagacgaaa gggcctcgtg atacgcctat ttttataggt    540
taatgtcatg ataataatgg tttcttagac gtgaggtggc acttttcggg gaaatgtgcg    600
cggaacccct atttgtttat ttttctaaat acattcaaat atgtatccgc tcatgagaca    660
ataaccctga taaatgcttc aataatattt tgttaaaatt cgcgttaaat ttttgttaaa    720
tcagctcatt ttttaaccaa taggccgaaa tcggcaaaat cccttataaa tcaaaagaat    780
agaccgagat agggttgagt gttgttccag tttggaacaa gagtccacta ttaaagaacg    840
tggactccaa cgtcaaaggg cgaaaaaccg tctatcaggg cgatggccca ctacgtgaac    900
catcacccta atcaagtttt tggggtcga ggtgccgtaa agcactaaat cggaacccta    960
aagggagccc ccgatttaga gcttgacggg gaaagccggc gaacgtggcg agaaaggaag   1020
ggaagaaagc gaaaggagcg ggcgctaggg cgctggcaag tgtagcggtc acgctgcgcg   1080
taaccaccac acccgccgcg cttaatgcgc cgctacaggg cgcgtcaggt ggcacttttc   1140
ggggaaatgt gcgcggaacc cctatttgtt tattttcta aatacattca aatatgtatc   1200
cgctcatgag acaataaccc tgataaatgc ttcaataata ttgaaaagg aagagtatga   1260 gtattcaaca tttccgtgtc gcccttattc ccttttttgc ggcattttgc cttcctgttt   1320
ttgctcaccc agaaacgctg gtgaaagtaa aagatgctga agatcagttg ggtgcacgag   1380
tgggttacat cgaactggat ctcaacagcg gtaagatcct tgagagtttt cgccccgaag   1440
aacgttttcc aatgatgagc actttaaag ttctgctatg tggcgcggta ttatcccgtg   1500
ttgacgccgg gcaagagcaa ctcggtcgcc gcatacacta ttctcagaat gacttggttg   1560
agtactcacc agtcacagaa aagcatctta cggatggcat gacagtaaga gaattatgca   1620
gtgctgccat aaccatgagt gataacactg cggccaactt acttctgaca acgatcggag   1680
gaccgaagga gctaaccgct tttttgcaca acatggggga tcatgtaact cgccttgatc   1740
gttgggaacc ggagctgaat gaagccatac caaacgacga gcgtgacacc acgatgcctg   1800
cagcaatggc aacaacgttg cgcaaactat taactggcga actacttact ctagcttccc   1860
ggcaacaatt aatagactgg atggaggcgg ataaagttgc aggaccactt ctgcgctcgg   1920
cccttccggc tggctggttt attgctgata atctggagc cggtgagcgt gggtctcgcg   1980
gtatcattgc agcactgggg ccagatggta agccctcccg tatcgtagtt atctacacga   2040
cggggagtca ggcaactatg gatgaacgaa atagacagat cgctgagata ggtgcctcac   2100
tgattaagca ttggtaactg tcagaccaag tttactcata tactttag attgatttaa   2160 aacttcattt ttaatttaaa aggatctagg tgaagatcct ttttgataat ctcatgacca   2220
aaatccctta acgtgagttt tcgttccact gagcgtcaga ccccgtagaa aagatcaaag   2280
gatcttcttg agatcctttt tttctgcgcg taatctgctg cttgcaaaca aaaaaaccac   2340
cgctaccagc ggtggtttgt ttgccggatc aagagctacc aactcttttt ccgaaggtaa   2400
ctggcttcag cagagcgcag ataccaaata ctgtccttct agtgtagccg tagttaggcc   2460
accacttcaa gaactctgta gcaccgccta catacctcgc tctgctaatc ctgttaccag   2520
```

-continued

| | |
|---|---|
| tggctgctgc cagtggcgat aagtcgtgtc ttaccgggtt ggactcaaga cgatagttac | 2580 |
| cggataaggc gcagcggtcg ggctgaacgg ggggttcgtg cacacagccc agcttggagc | 2640 |
| gaacgaccta caccgaactg agatacctac agcgtgagct atgagaaagc gccacgcttc | 2700 |
| ccgaagggag aaaggcggac aggtatccgg taagcggcag ggtcggaaca ggagagcgca | 2760 |
| cgagggagct tccaggggga aacgcctggt atctttatag tcctgtcggg tttcgccacc | 2820 |
| tctgacttga gcgtcgattt ttgtgatgct cgtcaggggg gcggagccta tggaaaaacg | 2880 |
| ccagcaacgc ggccttttta cggttcctgg ccttttgctg gccttttgct cacatgttct | 2940 |
| ttcctgcgtt atcccctgat tctgtggata accgtattac cgcctttgag tgagctgata | 3000 |
| ccgctcgccg cagccgaacg accgagcgca gcgagtcagt gagcgaggaa gcggaagagc | 3060 |
| gcctgatgcg gtattttctc cttacgcatc tgtgcggtat ttcacaccgc aatggtgcac | 3120 |
| tctcagtaca atctgctctg atgccgcata gttaagccag tatacactcc gctatcgcta | 3180 |
| cgtgactggg tcatggctgc gccccgacac ccgccaacac ccgctgacgc gccctgacgg | 3240 |
| gcttgtctgc tcccggcatc cgcttacaga caagctgtga ccgtctccgg agctgcatg | 3300 |
| tgtcagaggt tttcaccgtc atcaccgaaa cgcgcgaggc ag | 3342 |

<210> SEQ ID NO 23
<211> LENGTH: 3836
<212> TYPE: DNA
<213> ORGANISM: Artificial Sequence
<220> FEATURE:
<223> OTHER INFORMATION: pEX821 vector

<400> SEQUENCE: 23

| | |
|---|---|
| gatctcgatc ccgcgaaatt aatacgactc actataggga gaccacaacg gtttccctct | 60 |
| agaaataatt ttgtttaact ttaagaagga gatatacata tgaacgctgg tgtcactcag | 120 |
| accccaaaat tccaggtcct gaagacagga cagagcatga cactgcagtg tgcccaggat | 180 |
| atgaaccatg aatacatgtc ctggtatcga caagacccag gcatggggct gaggctgatt | 240 |
| cattactcag ttggtgctgg tatcactgac caaggagaag tccccaatgg ctacaatgtc | 300 |
| tccagatcaa ccacagagga tttcccgctc aggctgctgt cggctgctcc ctcccagaca | 360 |
| tctgtgtact ctgtgccag caggccggga ctagcgggag ggcgaccaga gcagtacttc | 420 |
| gggccgggca ccaggctcac ggtcacagag gacctgaaaa acgtgttccc acccgaggtc | 480 |
| gctgtgtttg agccatcaga agcagagatc tcccacaccc aaaaggccac actggtgtgc | 540 |
| ctggccaccg gttctacccc cgaccacgtg agctgagct ggtgggtgaa tgggaaggag | 600 |
| gtgcacagtg gggtctgcac agacccgcag cccctcaagg agcagcccgc cctcaatgac | 660 |
| tccagatacg ctctgagcag ccgcctgagg gtctcggcca ccttctggca ggaccccgc | 720 |
| aaccacttcc gctgtcaagt ccagttctac gggctctcgg agaatgacga gtggacccag | 780 |
| gatagggcca aacccgtcac ccagatcgtc agcgccgagg cctggggtag agcagactaa | 840 |
| gcttgaattc cgatccggct gctaacaaag cccgaaagga agctgagttg gctgctgcca | 900 |
| ccgctgagca ataactagca taaccccttg gggcctctaa acgggtcttg aggggttttt | 960 |
| tgctgaaagg aggaactata tccggataat tcttgaagac gaaagggcct cgtgatacgc | 1020 |
| ctatttttat aggttaatgt catgataata atggtttctt agacgtcagg tggcactttt | 1080 |
| cggggaaatg tgcgcggaac ccctatttgt ttatttttct aaatacattc aaatatgtat | 1140 |
| ccgctcatga caataaacc ctgataaatg cttcaataat attttgttaa aattcgcgtt | 1200 |
| aaatttttgt taaatcagct cattttttaa ccaataggcc gaaatcggca aaatccctta | 1260 |

```
taaatcaaaa gaatagaccg agatagggtt gagtgttgtt ccagtttgga acaagagtcc    1320
actattaaag aacgtggact ccaacgtcaa agggcgaaaa accgtctatc agggcgatgg    1380
cccactacgt gaaccatcac cctaatcaag ttttttgggg tcgaggtgcc gtaaagcact    1440
aaatcggaac cctaaaggga gcccccgatt tagagcttga cggggaaagc cggcgaacgt    1500
ggcgagaaag gaagggaaga aagcgaaagg agcgggcgct agggcgctgg caagtgtagc    1560
ggtcacgctg cgcgtaacca ccacacccgc cgcgcttaat gcgccgctac agggcgcgtc    1620
aggtggcact tttcggggaa atgtgcgcgg aacccctatt tgtttatttt tctaaataca    1680
ttcaaatatg tatccgctca tgagacaata accctgataa atgcttcaat aatattgaaa    1740
aaggaagagt atgagtattc aacatttccg tgtcgccctt attcccttt ttgcggcatt     1800 ttgccttcct gttttgtgctc acccagaaac gctggtgaaa gtaaaagatg ctgaagatca    1860
gttgggtgca cgagtgggtt acatcgaact ggatctcaac agcggtaaga tccttgagag    1920
ttttcgcccc gaagaacgtt ttccaatgat gagcactttt aaagttctgc tatgtggcgc    1980
ggtattatcc cgtgttgacg ccgggcaaga gcaactcggt cgccgcatac actattctca    2040
gaatgacttg gttgagtact caccagtcac agaaaagcat cttacggatg gcatgacagt    2100
aagagaatta tgcagtgctg ccataaccat gagtgataac actgcggcca acttacttct    2160
gacaacgatc ggaggaccga aggagctaac cgcttttttg cacaacatgg gggatcatgt    2220
aactcgcctt gatcgttggg aaccggagct gaatgaagcc ataccaaacg acgagcgtga    2280
caccacgatg cctgcagcaa tggcaacaac gttgcgcaaa ctattaactg gcgaactact    2340
tactctagct tcccggcaac aattaataga ctggatggag gcggataaag ttgcaggacc    2400
acttctgcgc tcggcccttc cggctggctg gtttattgct gataaatctg gagccggtga    2460
gcgtgggtct cgcggtatca ttgcagcact ggggccagat ggtaagccct cccgtatcgt    2520
agttatctac acgacgggga gtcaggcaac tatggatgaa cgaaatagac agatcgctga    2580
gataggtgcc tcactgatta agcattggta actgtcagac caagtttact catatatact    2640
ttagattgat ttaaaacttc atttttaatt taaaaggatc taggtgaaga tcctttttga    2700
taatctcatg accaaaatcc cttaacgtga gttttcgttc cactgagcgt cagacccgt     2760 agaaaagatc aaaggatctt cttgagatcc ttttttctg cgcgtaatct gctgcttgca     2820
aacaaaaaaa ccaccgctac cagcggtggt ttgtttgccg gatcaagagc taccaactct    2880
ttttccgaag gtaactggct tcagcagagc gcagatacca atactgtcc ttctagtgta     2940 gccgtagtta ggccaccact tcaagaactc tgtagcaccg cctacatacc tcgctctgct    3000
aatcctgtta ccagtggctg ctgccagtgg cgataagtcg tgtcttaccg ggttggactc    3060
aagacgatag ttaccggata aggcgcagcg gtcgggctga acggggggtt cgtgcacaca    3120
gcccagcttg gagcgaacga cctacaccga actgagatac ctacagcgtg agctatgaga    3180
aagcgccacg cttcccgaag ggagaaaggc ggacaggtat ccggtaagcg cagggtcgg     3240 aacaggagag cgcacgaggg agcttccagg gggaaacgcc tggtatcttt atagtcctgt    3300
cgggtttcgc cacctctgac ttgagcgtcg attttgtga tgctcgtcag ggggggcggag    3360 cctatggaaa aacgccagca acgcggcctt tttacggttc ctggccttt gctggccttt     3420 tgctcacatg ttcttcctg cgttatcccc tgattctgtg ataaccgta ttaccgcctt      3480 tgagtgagct gataccgctc gccgcagccg aacgaccgag cgcagcgagt cagtgagcga    3540
ggaagcggaa gagcgcctga tgcggtattt tctccttacg catctgtgcg gtatttcaca    3600
ccgcaatggt gcactctcag tacaatctgc tctgatgccg catagttaag ccagtataca    3660
```

```
ctccgctatc gctacgtgac tgggtcatgg ctgcgccccg acacccgcca acacccgctg    3720
acgcgccctg acgggcttgt ctgctcccgg catccgctta cagacaagct gtgaccgtct    3780
ccgggagctg catgtgtcag aggttttcac cgtcatcacc gaaacgcgcg aggcag         3836
```

<210> SEQ ID NO 24
<211> LENGTH: 378
<212> TYPE: PRT
<213> ORGANISM: Artificial Sequence
<220> FEATURE:
<223> OTHER INFORMATION: Truncated soluble parental GAG TCR beta chain
      containing an introduced Cys residue linked to WT IL-2 via a
      peptide linker

<400> SEQUENCE: 24

```
Met Glu Ala Gly Val Thr Gln Ser Pro Thr His Leu Ile Lys Thr Arg
1               5                   10                  15

Gly Gln Gln Val Thr Leu Arg Cys Ser Pro Lys Ser Gly His Asp Thr
            20                  25                  30

Val Ser Trp Tyr Gln Gln Ala Leu Gly Gln Gly Pro Gln Phe Ile Phe
        35                  40                  45

Gln Tyr Tyr Glu Glu Glu Arg Gln Arg Gly Asn Phe Pro Asp Arg
    50                  55                  60

Phe Ser Gly His Gln Phe Pro Asn Tyr Ser Ser Glu Leu Asn Val Asn
65                  70                  75                  80

Ala Leu Leu Leu Gly Asp Ser Ala Leu Tyr Leu Cys Ala Ser Ser Asp
                85                  90                  95

Thr Val Ser Tyr Glu Gln Tyr Phe Gly Pro Gly Thr Arg Leu Thr Val
            100                 105                 110

Thr Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Pro Gly Ala Pro Thr Ser Ser Thr Lys Lys Thr Gln
                245                 250                 255

Leu Gln Leu Glu His Leu Leu Leu Asp Leu Gln Met Ile Leu Asn Gly
            260                 265                 270

Ile Asn Asn Tyr Lys Asn Pro Lys Leu Thr Arg Met Leu Thr Phe Lys
        275                 280                 285

Phe Tyr Met Pro Lys Lys Ala Thr Glu Leu Lys His Leu Gln Cys Leu
    290                 295                 300

Glu Glu Glu Leu Lys Pro Leu Glu Glu Val Leu Asn Leu Ala Gln Ser
305                 310                 315                 320

Lys Asn Phe His Leu Arg Pro Arg Asp Leu Ile Ser Asn Ile Asn Val
                325                 330                 335
```

```
Ile Val Leu Glu Leu Lys Gly Ser Glu Thr Thr Phe Met Cys Glu Tyr
            340                 345                 350

Ala Asp Glu Thr Ala Thr Ile Val Glu Phe Leu Asn Arg Trp Ile Thr
            355                 360                 365

Phe Cys Gln Ser Ile Ile Ser Thr Leu Thr
            370                 375
```

<210> SEQ ID NO 25
<211> LENGTH: 822
<212> TYPE: DNA
<213> ORGANISM: Artificial Sequence
<220> FEATURE:
<223> OTHER INFORMATION: DNA encoding the full-length parental GAG TCR
      alpha chain codon optimised for human expression

<400> SEQUENCE: 25

```
atgatgaaga gcctgagggt gctgctggtg atcctgtggc tgcagctgtc ctgggtgtgg      60
agccagcaga aggaggtgga gcagaatagc ggccctctga gcgtgcccga gggcgccatc     120
gccagcctga actgtaccta cagcgacaga ggcagccaga gcttcttctg gtacaggcag     180
tacagcggca gagcccccga gctgattatg ttcatctaca gcaacggcga caaggaggac     240
ggcagattca ccgcccagct gaacaaggcc agccagtaca tcagcctgct gatccgggat     300
agcaagctgt ccgacagcgc cacctacctg tgtgccgtga aaccaatagc ggctacgcc      360 ctgaatttcg gcaagggcac cagcctgctg gtgacccccc acatccagaa tcctgacccc     420
gccgtgtacc agctgagaga cagcaagagc agcgacaaga gcgtgtgtct gttcaccgac     480
ttcgacagcc agaccaacgt gtcccagagc aaggacagcg acgtgtacat caccgacaag     540
accgtgctgg acatgaggag catggacttc aagagcaaca gcgccgtggc ctggagcaac     600
aagagcgact tcgcctgtgc caacgccttc aacaacagca tcatccccga ggacaccttt     660
ttccccagcc ctgagagcag ctgtgacgtg aaactggtgg agaagagctt cgagaccgac     720
accaacctga acttccagaa cctgagcgtg atcggcttca atcctgctg ctgaaggtg      780 gccggattca acctgctgat gaccctgaga ctgtggagca gc                         822
```

<210> SEQ ID NO 26
<211> LENGTH: 930
<212> TYPE: DNA
<213> ORGANISM: Artificial Sequence
<220> FEATURE:
<223> OTHER INFORMATION: DNA encoding the full-length parental GAG TCR
      beta chain codon optimised for human expression

<400> SEQUENCE: 26

```
atgggacccg gctgctgtgt ctgggccctg ctgtgcctgc tgggagccgg actggtggac      60
gccggagtga cccagagccc cacccacctg attaagacca ggggccagca ggtgacccctg    120 agatgtagcc ctaagagcgg ccacgatacc gtgtcctggt atcagcaggc cctgggccag     180
ggaccccagt tcatcttcca gtactacgag gaggaggaga ggcagagagg caacttcccc     240
gacagattca gcggccacca gttccccaat tacagcagcg agctgaacgt gaatgccctg     300
ctgctgggcg acagcgccct gtacctgtgt gccagcagcg acacagtgag ctacgagcag     360
tacttcggcc ctggcaccag actgaccgtg accgaggacc tgaagaacgt gttccctcct     420
gaggtggccg tgttcgagcc cagcgaggcc gagatcagcc acacccagaa ggccaccctg     480
gtgtgtctgg ccaccggctt ctaccccgac cacgtgagc tgtcctggtg ggtgaacggc      540
aaggaggtgc acagcggcgt gtccaccgac ccccagcccc tgaaggagca gcccgccctg     600
```

```
aacgatagca ggtactgcct gagcagcagg ctgagagtga gcgccacctt ctggcagaac      660
ccccggaacc acttcagatg ccaggtgcag ttctacggcc tgagcgagaa cgacgagtgg      720
acccaggata gagccaagcc cgtgacccag atcgtgtccg ccgaggcctg gggcagagcc      780
gactgtggct tcaccagcga gagctaccag cagggcgtgc tgtccgccac catcctgtac      840
gagatcctgc tgggcaaggc cacactgtac gccgtgctgg tgtccgccct ggtgctgatg      900
gctatggtga agcggaagga cagcaggggc                                       930

<210> SEQ ID NO 27
<211> LENGTH: 274
<212> TYPE: PRT
<213> ORGANISM: Artificial Sequence
<220> FEATURE:
<223> OTHER INFORMATION: Full-length parental GAG TCR alpha chain

<400> SEQUENCE: 27

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Ile Ser Leu
                85                  90                  95

Leu Ile Arg Asp Ser Lys Leu Ser Asp Ser Ala Thr Tyr Leu Cys Ala
            100                 105                 110

Val Arg Thr Asn Ser Gly Tyr Ala Leu Asn Phe Gly Lys Gly Thr Ser
        115                 120                 125

Leu Leu Val Thr Pro His Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 28
<211> LENGTH: 310
<212> TYPE: PRT
<213> ORGANISM: Artificial Sequence
```

```
<220> FEATURE:
<223> OTHER INFORMATION: Full-length parental GAG TCR beta chain

<400> SEQUENCE: 28

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Glu Leu Asn
                85                  90                  95

Val Asn Ala Leu Leu Leu Gly Asp Ser Ala Leu Tyr Leu Cys Ala Ser
            100                 105                 110

Ser Asp Thr Val Ser Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 29
<211> LENGTH: 207
<212> TYPE: PRT
<213> ORGANISM: Artificial Sequence
<220> FEATURE:
<223> OTHER INFORMATION: Alpha chain of a soluble high affinity c11c6
      GAG TCR containing an introduced Cys residue

<400> SEQUENCE: 29

Met Ala Gln Lys Glu Val Glu Gln Asn Ser Gly Pro Leu Ser Val Pro
1               5                   10                  15

Glu Gly Ala Ile Ala Ser Leu Asn Cys Thr Tyr Ser Asp Arg Gly Ser
```

```
                    20                  25                  30
Gln Ser Phe Phe Trp Tyr Arg Gln Tyr Ser Gly Lys Ser Pro Glu Leu
            35                  40                  45
Ile Met Phe Ile Tyr Ser Asn Gly Asp Lys Glu Asp Gly Arg Phe Thr
        50                  55                  60
Ala Gln Leu Asn Lys Ala Ser Gln Tyr Ile Ser Leu Leu Ile Arg Asp
65                  70                  75                  80
Ser Lys Leu Ser Asp Ser Ala Thr Tyr Leu Cys Ala Val Arg Gly Ala
                85                  90                  95
His Asp Tyr Ala Leu Asn Phe Gly Lys Gly Thr Ser Leu Leu Val Thr
            100                 105                 110
Pro His Ile Gln Asn Pro Asp Pro Ala Val Tyr Gln Leu Arg Asp Ser
        115                 120                 125
Lys Ser Ser Asp Lys Ser Val Cys Leu Phe Thr Asp Phe Asp Ser Gln
130                 135                 140
Thr Asn Val Ser Gln Ser Lys Asp Ser Asp Val Tyr Ile Thr Asp Lys
145                 150                 155                 160
Cys Val Leu Asp Met Arg Ser Met Asp Phe Lys Ser Asn Ser Ala Val
                165                 170                 175
Ala Trp Ser Asn Lys Ser Asp Phe Ala Cys Ala Asn Ala Phe Asn Asn
            180                 185                 190
Ser Ile Ile Pro Glu Asp Thr Phe Phe Pro Ser Pro Glu Ser Ser
        195                 200                 205

<210> SEQ ID NO 30
<211> LENGTH: 243
<212> TYPE: PRT
<213> ORGANISM: Artificial Sequence
<220> FEATURE:
<223> OTHER INFORMATION: Beta chain of a soluble high affinity c11c6
      GAG TCR containing an introduced Cys residue

<400> SEQUENCE: 30

Met Glu Ala Gly Val Thr Gln Ser Pro Thr His Leu Ile Lys Thr Arg
1               5                   10                  15
Gly Gln Gln Val Thr Leu Arg Cys Ser Pro Lys Ser Gly His Asp Thr
            20                  25                  30
Val Ser Trp Tyr Gln Gln Ala Leu Gly Gln Gly Pro Gln Phe Ile Phe
        35                  40                  45
Gln Tyr Ala Leu Gly Glu Glu Arg Gln Arg Gly Asn Phe Pro Asp Arg
    50                  55                  60
Phe Ser Gly His Gln Phe Pro Asn Tyr Ser Ser Glu Leu Asn Val Asn
65                  70                  75                  80
Ala Leu Leu Leu Gly Asp Ser Ala Leu Tyr Leu Cys Ala Ser Ser Asp
                85                  90                  95
Thr Val Ser Tyr Glu Gln Tyr Phe Gly Pro Gly Thr Arg Leu Thr Val
            100                 105                 110
Thr Glu Asp Leu Lys Asn Val Phe Pro Pro Glu Val Ala Val Phe Glu
        115                 120                 125
Pro Ser Glu Ala Glu Ile Ser His Thr Gln Lys Ala Thr Leu Val Cys
    130                 135                 140
Leu Ala Thr Gly Phe Tyr Pro Asp His Val Glu Leu Ser Trp Trp Val
145                 150                 155                 160
Asn Gly Lys Glu Val His Ser Gly Val Cys Thr Asp Pro Gln Pro Leu
                165                 170                 175
Lys Glu Gln Pro Ala Leu Asn Asp Ser Arg Tyr Ala Leu Ser Ser Arg
```

-continued

```
                    180                 185                 190
Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp

<210> SEQ ID NO 31
<211> LENGTH: 18
<212> TYPE: PRT
<213> ORGANISM: Foot-and-mouth disease virus

<400> SEQUENCE: 31

Leu Leu Asn Phe Asp Leu Leu Lys Leu Ala Gly Asp Val Glu Ser Asn
1               5                   10                  15

Pro Gly
```

HIGH AFFINITY HIV T CELL RECEPTORS

This application is a National Stage application of co-pending PCT application PCT/GB2006/001147 filed on Mar. 29, 2006, which was published in English under PCT Article 21(2) on Oct. 5, 2006, and which claims the benefit of GB 0506760.8 filed Apr. 1, 2005 and GB 0516487.6 filed Aug. 10, 2005. These applications are incorporated herein by reference in their entireties.

The present invention relates to T-cell receptors (TCRs) having the property of binding to HIV Gag polypeptide-derived SLYNTVATL-HLA-A*0201. The TCRs comprise at least one TCR α chain variable domain and/or at least one TCR β chain variable domain and have a $K_D$ for the said SLYNTVATL-HLA-A*0201 complex of less than or equal to 1 μM and/or has an off-rate ($k_{off}$) for the SLYNTVATL-HLA-A*0201 complex of $1 \times 10^{-3}$ $S^{-1}$ or slower.

BACKGROUND TO THE INVENTION

The Human Immuno-deficiency Virus (HIV) is the causative agent of Acquired Immuno-deficiency Disease Syndrome (AIDS). The virus is an enveloped retrovirus belonging to the lentivirus group. The SLYNTVATL (SEQ ID NO: 16) peptide is derived from the g17 gene product of the Gag gene, one of nine genes which make up the Human Immuno-deficiency Virus-1 (HIV-1) The peptide is loaded by HLA-A*0201 and presented on the surface of HIV infected cells. Therefore, the SLYNTVATL-HLA-A2*0201 complex provides an HIV marker that TCRs can target, for example for the purpose of delivering cytotoxic or immuno-stimulatory agents to the infected cells. However, for that purpose it would be desirable if the TCR had a high affinity and/or a slow off-rate for the peptide-HLA complex.

BRIEF DESCRIPTION OF THE INVENTION

This invention makes available for the first time TCRs having an affinity ($K_D$) of less than or equal to 1 μM, and/or an off-rate ($k_{off}$) of $1 \times 10^{-3}$ $S^{-1}$ or slower, for the SLYNTVATL-HLA-A*0201 complex PROVIDED THAT when the said TCR is presented by cell and comprises SEQ ID NOs: 1 and 2, the cell is not a native T cell. Such TCRs are useful, either alone or associated with a therapeutic agent, for targeting HIV infected cells presenting that complex

DETAILED DESCRIPTION OF THE INVENTION

The present invention provides a T-cell receptor (TCR) having the property of binding to SLYNTVATL-HLA-A*0201 and comprising at least one TCR α chain variable domain and/or at least one TCR β chain variable domain CHARACTERISED IN THAT said TCR has a $K_D$ for the said SLYNTVATL-HLA-A*0201 complex of less than or equal to 1 M and/or has an off-rate ($k_{off}$) for the SLYNTVATL-HLA-A*0201 complex of $1 \times 10^{-3}$ $S^{-1}$ or slower, PROVIDED THAT when the said TCR is presented by cell and comprises SEQ ID NOs: 1 and 2, the cell is not a native T cell. The $K_D$ and/or ($k_{off}$) measurement can be made by any of the known methods. A preferred method is the Surface Plasmon Resonance (Biacore) method of Example 4.

For comparison, the interaction of a disulfide-linked soluble variant of the parental HIV gag TCR (see SEQ ID NO: 9 for TCR α chain and SEQ ID NO: 10 for TCR β chain) and the SLYNTVATL-HLA-A*0201 complex has a $K_D$ of approximately 85 nM and an off-rate ($k_{off}$) of $2.21 \times 10^{-2}$ $S^{-1}$ as measured by the Biacore-base method of Example 4.

The parental HIV Gag TCR specific for the SLYNTVATL-HLA-A*0201 complex has the following Valpha chain and Vbeta chain gene usage:
Alpha chain—TRAV12.2
Beta chain:—TRBV 5.6

The parental HIV Gag TCR can be used as a template from which other TCRs of the invention with high affinity and/or a slow off-rate for the interaction between said TCRs and the SLYNTVATL-HLA-A*0201 complex can be produced. Thus the invention includes TCRs which are mutated relative to the parental HIV Gag TCR α chain variable domain (see FIG. 1a and SEQ ID No: 1) and/or β chain variable domain (see FIG. 1b and SEQ ID NO: 2) in at least one complementarity determining region (CDR) and/or variable domain framework region thereof. It is also contemplated that other hypervariable regions in the variable domains of the TCRs of the invention, such as the hypervariable 4 (HV4) regions, may be mutated within a high affinity mutant TCR.

Phage display provides one means by which libraries of TCR variants can be generated. Methods suitable for the phage display and subsequent screening of libraries of TCR variants each containing a non-native disulfide interchain bond are detailed in (Li et al., (2005) *Nature Biotech* 23 (3): 349-354) and WO 2004/04404.

Native TCRs exist in heterodimeric αβ or γδ forms. However, recombinant TCRs consisting of a single TCR α or TCR β chain have previously been shown to bind to peptide MHC molecules.

In one embodiment the TCR of the invention comprise both an α chain variable domain and an TCR β chain variable domain.

As will be obvious to those skilled in the art the mutation(s) in the TCR α chain sequence and/or TCR β chain sequence may be one or more of substitution(s), deletion(s) or insertion(s). These mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) mutagenesis and restriction enzyme-based cloning see (Sambrook & Russell, (2001) Molecular Cloning—A Laboratory Manual (3rd Ed.) CSHL Press) Further information on LIC procedures can be found in (Rashtchian, (1995) *Curr Opin Biotechnol* 6 (1): 30-6)

It should be noted that any αβ TCR that comprises similar Valpha and Vbeta gene usage and therefore amino acid sequence to that of the HIV Gag TCR could make a convenient template TCR. It would then be possible to introduce into the DNA encoding one or both of the variable domains of the template αβ TCR the changes required to produce the mutated high affinity TCRs of the invention. As will be obvious to those skilled in the art, the necessary mutations could be introduced by a number of methods, for example site-directed mutagenesis.

The TCRs of the invention include those in which one or more of the TCR alpha chain variable domain amino acids corresponding to those listed below are mutated relative to the amino acid occurring at these positions in the sequence provided for the parental HIV Gag TCR alpha chain variable domain in FIG. 1a and SEQ ID No: 1.

Unless stated to the contrary, the TCR amino acid sequences herein are generally provided including an N-terminal methionine (Met or M) residue. As will be known to those skilled in the art this residue may be removed during the production of recombinant proteins. As will also be obvious to those skilled in the art, it may be possible to truncate the sequences provided at the C-terminus and/or N-terminus thereof, by 1, 2, 3, 4, 5 or more residues, without substantially affecting the pMHC binding characteristics of the TCR, all such trivial variants are encompassed by the present invention.

As used herein the term "variable region" is understood to encompass all amino acids of a given TCR which are not included within the constant domain as encoded by the TRAC gene for TCR α chains and either the TRBC1 or TRBC2 genes for TCR β chains. (T cell receptor Factsbook, (2001) LeFranc and LeFranc, Academic Press, ISBN 0-12-441352-8)

As used herein the term "variable domain" is understood to encompass all amino acids of a given TCR which are encoded by a TRAV gene for TCR α chains and a TRBV gene for TCR β chains. (T cell receptor Factsbook, (2001) LeFranc and LeFranc, Academic Press, ISBN 0-12-441352-8)

As is known to those skilled in the art, part of the diversity of the TCR repertoire is due to variations which occur in the amino acid encoded by the codon at the boundary between the variable region, as defined herein, and the constant domain. For example, the codon that is present at this boundary in the parental HIV Gag TCR sequence results in the presence of the Histidine (H) residue at the C-terminal of the variable region sequences herein. This Histidine replaces the N-terminal Asparagine (N) residue encoded by the TRAC gene shown in FIG. 8a.

Embodiments of the invention include mutated TCRs which comprise mutation of one or more of alpha chain variable region amino acids corresponding to: 95T, 96N, 97S, 98G, and 100A, for example the amino acids:

95S or G
96A
97H
98D
100S

The numbering used above is the same as that shown in FIG. 1a and SEQ ID No: 1

Embodiments of the invention also include TCRs which comprise mutation of one or more of the TCR beta chain variable region amino acids corresponding to those listed below, are relative to the amino acid occurring at these positions in the sequence provided for the native HIV Gag TCR alpha chain variable region of the native HIV Gag TCR beta chain in FIG. 1b and SEQ ID No: 2. The amino acids referred to which may be mutated are: 51Y, 52E, 53E and 54E, for example:

51V or A
52R or L
53G
54V

The numbering used above is the same as that shown in FIG. 1b and SEQ ID No: 2

Further preferred embodiments of the invention are provided by TCRs comprising one of the mutated alpha chain variable region amino acid sequences shown in FIG. 6 (SEQ ID Nos: 11 to 13). Phenotypically silent variants of such TCRs also form part of this invention.

Additional preferred embodiments of the invention are provided by TCRs comprising one of the mutated beta chain variable region amino acid sequences shown in FIG. 7. (SEQ ID Nos: 14 and 15). Phenotypically silent variants of such TCRs also form part of this invention.

Native TCRs exist in heterodimeric αβ or γδ forms. However, recombinant TCRs consisting of αα or ββ homodimers have previously been shown to bind to peptide MHC molecules. Therefore, one embodiment of the invention is provided by TCR αα or TCR ββ homodimers.

Further preferred embodiments are provided by TCRs of the invention comprising the alpha chain variable region amino acid sequence and the beta chain variable region amino acid sequence combinations listed below, phenotypically silent variants of such TCRs also form part of this invention:

| Alpha chain variable region sequence, SEQ ID NO: | Beta chain variable region sequence, SEQ ID NO: |
|---|---|
| 1 | 2 |
| 1 | 14 |
| 1 | 15 |
| 11 | 2 |
| 12 | 2 |
| 13 | 2 |
| 12 | 15 |
| 13 | 15 |
| 12 | 14 |
| 13 | 14 |

In another preferred embodiment TCRs of the invention comprising the variable region combinations detailed above further comprise the alpha chain constant domain amino acid sequence shown in FIG. 8a (SEQ ID NO: 19) and one of the beta chain amino acid constant domain sequences shown in FIGS. 8b and 8c (SEQ ID NOs: 20 and 21) or phenotypically silent variants thereof.

As used herein the term "phenotypically silent variants" is understood to refer to those TCRs which have a $K_D$ for the said SLYNTVATL-HLA-A*0201 complex of less than or equal to 1 µM and/or have an off-rate ($k_{off}$) of $1 \times 10^{-3}$ $S^{-1}$ or slower. For example, as is known to those skilled in the art, it may be possible to produce TCRs that incorporate minor changes in the constant domain and/or variable regions thereof compared to those detailed above without altering the affinity and/or off-rate for the interaction with the SLYNTVATL-HLA-A*0201 complex. Such trivial variants are included in the scope of this invention. Those TCRs in which one or more conservative substitutions have been made also form part of this invention.

In one broad aspect, the TCRs of the invention are in the form of either single chain TCRs (scTCRs) or dimeric TCRs (dTCRs) as described in WO 04/033685 and WO 03/020763.

A suitable scTCR form comprises a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

Alternatively the first segment may be constituted by an amino acid sequence corresponding to a TCR β chain variable region, the second segment may be constituted by an amino acid sequence corresponding to a TCR α chain variable region sequence fused to the N terminus of an amino acid sequence corresponding to a TCR α chain constant domain extracellular sequence The above scTCRs may further comprise a disulfide bond between the first and second chains, said disulfide bond being one which has no equivalent in native αβT cell receptors, and wherein the length of the linker sequence and the position of the disulfide bond being such that the variable domain sequences of the first and second segments are mutually orientated substantially as in native αβT cell receptors.

More specifically the first segment may be constituted by an amino acid sequence corresponding to a TCR α chain variable region sequence fused to the N terminus of an amino acid sequence corresponding to a TCR α chain constant domain extracellular sequence, the second segment may be constituted by an amino acid sequence corresponding to a TCR β chain variable region fused to the N terminus of an amino acid sequence corresponding to TCR β chain constant domain extracellular sequence, and a disulfide bond may be provided between the first and second chains, said disulfide bond being one which has no equivalent in native αβ T cell receptors.

In the above scTCR forms, the linker sequence may link the C terminus of the first segment to the N terminus of the second segment, and may have the formula -PGGG-(SGGGG)$_n$-P- wherein n is 5 or 6 and P is proline, G is glycine and S is serine.

```
                                        (SEQ ID NO: 17)
-PGGG-SGGGGSGGGGSGGGGSGGGGSGGGG-P (SEQ ID NO: 18)
-PGGG-SGGGGSGGGGSGGGGSGGGGSGGGGSGGGG-P
```

A suitable dTCR form of the TCRs of the present invention comprises a first polypeptide wherein a sequence corresponding to a TCR α chain variable region sequence is fused to the N terminus of a sequence corresponding to a TCR α chain constant domain extracellular sequence, and a second polypeptide wherein a sequence corresponding to a TCR β chain variable region sequence fused to the N terminus a sequence corresponding to a TCR β chain constant domain extracellular sequence, the first and second polypeptides being linked by a disulfide bond which has no equivalent in native αβ T cell receptors.

The first polypeptide may comprise a TCR α chain variable region sequence is fused to the N terminus of a sequence corresponding to a TCR α chain constant domain extracellular sequence, and a second polypeptide wherein a sequence corresponding to a TCR β chain variable region sequence is fused to the N terminus a sequence corresponding to a TCR β chain constant domain extracellular sequence, the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof. ("TRAC" etc. nomenclature herein as per T cell receptor Factsbook, (2001) LeFranc and LeFranc, Academic Press, ISBN 0-12-441352-8)

The dTCR or scTCR form of the TCRs of the invention may have amino acid sequences corresponding to human αβ TCR extracellular constant domain and variable region sequences, and a disulfide bond may link amino acid residues of the said constant domain sequences, which disulfide bond has no equivalent in native TCRs. The disulfide bond is between cysteine residues corresponding to amino acid residues whose β carbon atoms are less than 0.6 nm apart in native TCRs, for example between cysteine residues substituted for Thr 48 of exon 1 of TRAC*01 and Ser 57 of exon 1 of TRBC1*01 or TRBC2*01 or the non-human equivalent thereof. Other sites where cysteines can be introduced to form the disulfide bond are the following residues in exon 1 of TRAC*01 for the TCR α chain and TRBC1*01 or TRBC2*01 for the TCR β chain:

| TCR α chain | TCR β chain | Native β carbon separation (nm) |
|---|---|---|
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

In addition to the non-native disulfide bond referred to above, the dTCR or scTCR form of the TCRs of the invention may include a disulfide bond between residues corresponding to those linked by a disulfide bond in native TCRs.

The dTCR or scTCR form of the TCRs of the invention preferably does not contain a sequence corresponding to transmembrane or cytoplasmic sequences of native TCRs.

TCRs of the invention bind strongly to the SLYNTVATL-HLA-A2*0201. These TCRs also bind to an altered, but still useful, extent to naturally occurring variants of the HIV Gag-derived SLYNTVATL when loaded by HLA-A*0201. Variants of the SLYNTVATL which have been isolated from AIDs patients include the following (Sewell et al., (1997) *Eur J Immunol.* 27: 2323-2329):

```
SLFNTVATL

SLFNTVAVL

SLSNTVATL

SSFNTVATL

SLLNTVATL

SLYNTIATL

SLYNTIAVL

SLFNTIATL

SLFNTIAVL

SLFNFVATL
```

The mutated amino acids are underlined.

PEGylated TCR Monomers

In one particular embodiment a TCR of the invention is associated with at least one polyalkylene glycol chain(s). This association may be cause in a number of ways known to those skilled in the art. In a preferred embodiment the polyalkylene chain(s) is/are covalently linked to the TCR. In a further embodiment the polyethylene glycol chains of the present aspect of the invention comprise at least two polyethylene repeating units.

Multivalent TCR Complexes

One aspect of the invention provides a multivalent TCR complex comprising at least two TCRs of the invention. In one embodiment of this aspect, at least two TCR molecules are linked via linker moieties to form multivalent complexes. Preferably the complexes are water soluble, so the linker moiety should be selected accordingly. Furthermore, it is preferable that the linker moiety should be capable of attachment to defined positions on the TCR molecules, so that the structural diversity of the complexes formed is minimised. One embodiment of the present aspect is provided by a TCR complex of the invention wherein the polymer chain or peptidic linker sequence extends between amino acid residues of each TCR which are not located in a variable region sequence of the TCR.

Since the complexes of the invention may be for use in medicine, the linker moieties should be chosen with due regard to their pharmaceutical suitability, for example their immunogenicity.

Examples of linker moieties which fulfil the above desirable criteria are known in the art, for example the art of linking antibody fragments.

There are two classes of linker that are preferred for use in the production of multivalent TCR molecules of the present invention. A TCR complex of the invention in which the TCRs are linked by a polyalkylene glycol chain provides one embodiment of the present aspect.

The first are hydrophilic polymers such as polyalkylene glycols. The most commonly used of this class are based on polyethylene glycol or PEG, the structure of which is shown below.

Wherein n is greater than two. However, others are based on other suitable, optionally substituted, polyalkylene glycols include polypropylene glycol, and copolymers of ethylene glycol and propylene glycol.

Such polymers may be used to treat or conjugate therapeutic agents, particularly polypeptide or protein therapeutics, to achieve beneficial changes to the PK profile of the therapeutic, for example reduced renal clearance, improved plasma half-life, reduced immunogenicity, and improved solubility. Such improvements in the PK profile of the PEG-therapeutic conjugate are believe to result from the PEG molecule or molecules forming a 'shell' around the therapeutic which sterically hinders the reaction with the immune system and reduces proteolytic degradation. (Casey et al, (2000) Tumor Targetting 4 235-244) The size of the hydrophilic polymer used my in particular be selected on the basis of the intended therapeutic use of the TCR complex. There are numerous review papers and books that detail the use of PEG and similar molecules in pharmaceutical formulations. For example, see Harris (1992) Polyethylene Glycol Chemistry—Biotechnical and Biomedical Applications, Plenum, New York, N.Y. or Harris & Zalipsky (1997) Chemistry and Biological Applications of Polyethylene Glycol ACS Books, Washington, D.C.

The polymer used can have a linear or branched conformation. Branched PEG molecules, or derivatives thereof, can be induced by the addition of branching moieties including glycerol and glycerol oligomers, pentaerythritol, sorbitol and lysine.

Usually, the polymer will have a chemically reactive group or groups in its structure, for example at one or both termini, and/or on branches from the backbone, to enable the polymer to link to target sites in the TCR. This chemically reactive group or groups may be attached directly to the hydrophilic polymer, or there may be a spacer group/moiety between the hydrophilic polymer and the reactive chemistry as shown below:

Reactive chemistry-Hydrophilic polymer-Reactive chemistry

Reactive chemistry-Spacer-Hydrophilic polymer-Spacer-Reactive chemistry

The spacer used in the formation of constructs of the type outlined above may be any organic moiety that is a non-reactive, chemically stable, chain, Such spacers include, by are not limited to the following:

—$(CH_2)_n$— wherein n=2 to 5
—$(CH_2)_3 NHCO(CH_2)_2$

A TCR complex of the invention in which a divalent allylene spacer radical is located between the polyalkylene glycol chain and its point of attachment to a TCR of the complex provides a further embodiment of the present aspect.

A TCR complex of the invention in which the polyalkylene glycol chain comprises at least two polyethylene glycol repeating units provides a further embodiment of the present aspect.

There are a number of commercial suppliers of hydrophilic polymers linked, directly or via a spacer, to reactive chemistries that may be of use in the present invention. These suppliers include Nektar Therapeutics (CA, USA), NOF Corporation (Japan), Sunbio (South Korea) and Enzon Pharmaceuticals (NJ, USA).

Commercially available hydrophilic polymers linked, directly or via a spacer, to reactive chemistries that may be of use in the present invention include, but are not limited to, the following:

| PEG linker Description | Source of PEG | Catalogue Number |
|---|---|---|
| TCR Monomer attachment | | |
| 5K linear (Maleimide) | Nektar | 2D2MOHO1 |
| 20K linear (Maleimide) | Nektar | 2D2MOPO1 |
| 20K linear (Maleimide) | NOF Corporation | SUNBRIGHT ME-200MA |
| 20K branched (Maleimide) | NOF Corporation | SUNBRIGHT GL2-200MA |
| 30K linear (Maleimide) | NOF Corporation | SUNBRIGHT ME-300MA |
| 40K branched PEG (Maleimide) | Nektar | 2D3XOTO1 |
| 5K-NP linear (for Lys attachment) | NOF Corporation | SUNBRIGHT MENP-50H |
| 10K-NP linear (for Lys attachment) | NOF Corporation | SUNBRIGHT MENP-10T |
| 20K-NP linear (for Lys attachment) | NOF Corporation | SUNBRIGHT MENP-20T |
| TCR dimer linkers | | |
| 3.4K linear (Maleimide) | Nektar | 2D2DOFO2 |
| 5K forked (Maleimide) | Nektar | 2D2DOHOF |
| 10K linear (with orthopyridyl ds-linkers in place of Maleimide) | Sunbio | |
| 20K forked (Maleimide) | Nektar | 2D2DOPOF |
| 20K linear (Maleimide) | NOF Corporation | |
| 40K forked (Maleimide) | Nektar | 2D3XOTOF |
| Higher order TCR multimers | | |
| 15K, 3 arms, $Mal_3$ (for trimer) | Nektar | OJOONO3 |
| 20K, 4 arms, $Mal_4$ (for tetramer) | Nektar | OJOOPO4 |
| 40K, 8 arms, $Mal_8$ (for octamer) | Nektar | OJOOTO8 |

A wide variety of coupling chemistries can be used to couple polymer molecules to protein and peptide therapeutics. The choice of the most appropriate coupling chemistry is largely dependant on the desired coupling site. For example, the following coupling chemistries have been used attached to one or more of the termini of PEG molecules (Source: Nektar Molecular Engineering Catalogue 2003):

N-maleimide
Vinyl sulfone
Benzotriazole carbonate
Succinimidyl proprionate
Succinimidyl butanoate
Thio-ester
Acetaldehydes
Acrylates
Biotin
Primary amines As stated above non-PEG based polymers also provide suitable linkers for multimerising the TCRs of the present invention. For example, moieties containing maleimide termini linked by aliphatic chains such as BMH and BMOE (Pierce, products Nos. 22330 and 22323) can be used.

Peptidic linkers are the other class of TCR linkers. These linkers are comprised of chains of amino acids, and function to produce simple linkers or multimerisation domains onto which TCR molecules can be attached. The biotin/streptavidin system has previously been used to produce TCR tetramers (see WO/99/60119) for in-vitro binding studies. However, strepavidin is a microbially-derived polypeptide and as such not ideally suited to use in a therapeutic.

A TCR complex of the invention in which the TCRs are linked by a peptidic linker derived from a human multimerisation domain provides a further embodiment of the present aspect.

There are a number of human proteins that contain a multimerisation domain that could be used in the production of multivalent TCR complexes. For example the tetramerisation domain of p53 which has been utilised to produce tetramers of scFv antibody fragments which exhibited increased serum persistence and significantly reduced off-rate compared to the monomeric scFV fragment. (Willuda et al. (2001) J. Biol. Chem. 276 (17) 14385-14392) Haemoglobin also has a tetramerisation domain that could potentially be used for this kind of application.

A multivalent TCR complex of the invention comprising at least two TCRs provides a final embodiment of this aspect, wherein at least one of said TCRs is associated with a therapeutic agent.

In one aspect a TCR (or multivalent complex thereof) of the present invention may alternatively or additionally comprise a reactive cysteine at the C-terminal or N-terminal of the alpha or beta chains thereof.

Diagnostic and Therapeutic Use

In one aspect the TCR of the invention may be associated with a therapeutic agent or detectable moiety. For example, said therapeutic agent or detectable moiety may be covalently linked to the TCR.

In one embodiment of the invention said therapeutic agent or detectable moiety is covalently linked to the C-terminus of one or both TCR chains.

In one aspect the scTCR or one or both of the dTCR chains of TCRs of the present invention may be labelled with an detectable moiety, for example a label that is suitable for diagnostic purposes. Such labelled TCRs are useful in a method for detecting a SLYNTVATL-HLA-A*0201 complex which method comprises contacting the TCR ligand with a TCR (or a multimeric high affinity TCR complex) which is specific for the TCR ligand; and detecting binding to the TCR ligand. In tetrameric TCR complexes formed for example, using biotinylated heterodimers, fluorescent streptavidin can be used to provide a detectable label. Such a fluorescently-labelled TCR tetramer is suitable for use in FACS analysis, for example to detect antigen presenting cells carrying the SLYNTVATL-HLA-A*0201 complex for which these high affinity TCRs are specific.

Another manner in which the soluble TCRs of the present invention may be detected is by the use of TCR-specific antibodies, in particular monoclonal antibodies. There are many commercially available anti-TCR antibodies, such as αF1 and βF1, which recognise the constant domains of the α and β chains, respectively.

In a further aspect a TCR (or multivalent complex thereof) of the present invention may alternatively or additionally be associated with (e.g. covalently or otherwise linked to) a therapeutic agent which may be, for example, a toxic moiety for use in cell killing, or an immune effector molecule such as an interleukin or a cytokine. A multivalent TCR complex of the invention may have enhanced binding capability for a TCR ligand compared to a non-multimeric wild-type or T cell receptor heterodimer of the invention. Thus, the multivalent TCR complexes according to the invention are particularly useful for tracking or targeting cells presenting SLYNTVATL-HLA-A*0201 complexes in vitro or in vivo, and are also useful as intermediates for the production of further multivalent TCR complexes having such uses. These TCRs or multivalent TCR complexes may therefore be provided in a pharmaceutically acceptable formulation for use in vivo.

The invention also provides a method for delivering a therapeutic agent to a target cell, which method comprises contacting potential target cells with a TCR or multivalent TCR complex in accordance with the invention under conditions to allow attachment of the TCR or multivalent TCR complex to the target cell, said TCR or multivalent TCR complex being specific for the SLYNTVATL-HLA-A*0201 complex and having the therapeutic agent associated therewith.

In particular, the soluble TCR or multivalent TCR complex of the present invention can be used to deliver therapeutic agents to the location of cells presenting a particular antigen. This would be useful in many situations and, in particular, against HIV infected cells. A therapeutic agent could be delivered such that it would exercise its effect locally but not only on the cell it binds to. Thus, one particular strategy envisages cytotoxic or immuno-stimulatory molecules linked to TCRs or multivalent TCR complexes according to the invention specific for the SLYNTVATL-HLA-A*0201 complex.

Many therapeutic agents could be employed for this use, for instance radioactive compounds, enzymes (perforin for example) or chemotherapeutic agents (cis-platin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the TCR to the relevant antigen presenting cells.

Other suitable therapeutic agents include:
small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;

peptide cytotoxins, i.e. proteins or fragments thereof with the ability to kill mammalian cells. Including but not limited to, ricin, diphtheria toxin, pseudomonas bacterial exotoxin A, DNAase and RNAase;

radio-nuclides, i.e. unstable isotopes of elements which decay with the concurrent emission of one or more of α or β particles, or γ rays. including but not limited to, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

prodrugs, including but not limited to, antibody directed enzyme pro-drugs;

immuno-stimulants, i.e. moieties which stimulate immune response. Including but not limited to, cytokines such as IL-2 and IFN, Superantigens and mutants thereof, TCR-HLA fusions and chemokines such as IL-8, platelet factor 4, melanoma growth stimulatory protein, etc, antibodies or fragments thereof, complement activators, xenogeneic protein domains, allogeneic protein domains, viral/bacterial protein domains, viral/bacterial peptides and anti-T cell determinant antibodies (e.g. anti-CD3 or anti-CD28) or antibody analogues such as Nanobodies™ and Affybodies™.

Soluble TCRs or multivalent TCR complexes of the invention may be linked to an enzyme capable of converting a prodrug to a drug. This allows the prodrug to be converted to the drug only at the site where it is required (i.e. targeted by the sTCR).

It is expected that the high affinity SLYNTVATL (SEQ ID NO: 16)-HLA-A*0201 specific TCRs disclosed herein may be used in methods for the diagnosis and treatment of AIDS.

For treatment, therapeutic agent localisation in the vicinity of HIV infected (CD4$^+$) cells would enhance the effect of toxins or immunostimulants. For vaccine delivery, the vaccine antigen could be localised in the vicinity of antigen presenting cells, thus enhancing the efficacy of the antigen. The method can also be applied for imaging purposes.

One embodiment is provided by a membrane preparation comprising a TCR of the invention. Said membrane preparation may be prepared from cells or may comprise a synthetic membrane.

Another embodiment is provided by a cell harbouring an expression vector comprising nucleic acid encoding a TCR of the invention. For example, said cell may be a T cell.

Further embodiments of the invention are provided by a pharmaceutical composition comprising:

a TCR or a multivalent TCR complex of the invention (optionally associated with a therapeutic agent), or a membrane preparation comprising a TCR of the invention, or a plurality of cells harbouring an expression vector comprising nucleic acid encoding a TCR of the invention, together with a pharmaceutically acceptable carrier;

The invention also provides a method of treatment of AIDS comprising administering to a subject suffering such AIDS an effective amount of a TCR or a multivalent TCR complex of the invention, or a membrane preparation comprising a TCR of the invention, or a plurality of cells harbouring an expression vector comprising nucleic acid encoding a TCR of the invention. In a related embodiment the invention provides for the use of a TCR or a multivalent TCR complex of the invention, or a membrane preparation comprising a TCR of the invention, or a plurality of cells harbouring an expression vector comprising nucleic acid encoding a TCR of the invention, in the preparation of a composition for the treatment of AIDS. Further specific embodiments of these uses and methods of the invention are provided wherein the TCR, or multivalent TCR complex of the invention, or a membrane preparation comprising a TCR of the invention is administered in a form which is associated with a therapeutic agent. In other preferred embodiments the cells harbouring an expression vector comprising nucleic acid encoding a TCR of the invention are CD8$^+$ T cells.

Therapeutic or imaging TCRs in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

Without wishing to be limited by theory, it is expected that the TCRs of the invention will provide effective targeting agents capable of delivering therapeutic agents such as immunostimulants and/or cytotoxic agents to HIV infected (CD4$^+$) cells. In particular, it is expected that the administration of the TCRs of the present invention when associated with immunostimulants and/or cytotoxic agents in combination with conventional anti-retrovirus drug therapies and/or IL-2 treatment will be able to target HIV infected cells.

The following is a list of anti-retroviral drugs currently approved for use in the US:

Agenerase (amprenavir)—protease inhibitor

Combivir—combination of Retrovir (300 mg) and Epivir (150 mg)

Crixivan (indinavir)—protease inhibitor

Epivir (3tc/lamivudine)—nucleoside analog reverse transcriptase inhibitor

Epzicom (a combination of 2 nucleoside reverse transcriptase inhibitors (NRTIs in the same pill; 600 mg of Ziagen (abacavir) and 300 mg of Epivir (3TC).

Emtriva [emtricitabine (FTC)]

Fortovase (saquinavir)—protease inhibitor

Fuzeon (enfuvirtide)—Fusion inhibitor

Hivid (ddc/zalcitabine)—nucleoside analog reverse transcriptase inhibitor

Invirase (saquinavir)—protease inhibitor

Kaletra (lopinavir)—protease inhibitor

Lexiva (Fosamprenavir)—Protease Inhibitor approved Oct. 20, 2003

Norvir (ritonavir)—protease inhibitor

Rescriptor (delavirdine)—non nucleoside analog reverse transcriptase inhibitor

Retrovir, AZT (zidovudine)—nucleoside analog reverse transcriptase inhibitor

Reyataz (atazanavir; BMS-232632)—protease inhibitor

Sustiva (efavirenz)—non nucleoside analog reverse transcriptase inhibitor

Trizivir (3 non nucleosides in one tablet; abacavir+zidovudine+lamivudine

Truvada (Emtricitabine+Tenofovir DF)

Videx (ddI/didanosine) nucleoside analog reverse transcriptase inhibitor

Videx EC; (ddI/didanosine) nucleoside analog reverse transcriptase inhibitor;

Viracept (nelfinavir)—protease inhibitor

Viramune (nevirapine)—non nucleoside analog Reverse transcriptase inhibitor

Viread (tenofovir disoproxil fumarate) Nucleotide Reverse transcriptase inhibitor (Adenosine Class)

Zerit (d4t/stavudine)—nucleoside analog reverse transcriptase inhibitor

Ziagen (abacavir)—nucleoside analog reverse transcriptase inhibitor

The pharmaceutical composition may be adapted for administration by any appropriate route, for example parenteral, transdermal or via inhalation, preferably a parenteral (including subcutaneous, intramuscular, or, most preferably intravenous) route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

Additional Aspects

A scTCR or dTCR (which preferably is constituted by constant and variable sequences corresponding to human sequences) of the present invention may be provided in substantially pure form, or as a purified or isolated preparation. For example, it may be provided in a form which is substantially free of other proteins.

The sequence(s) of the nucleic acid or nucleic acids encoding the TCRs of the invention may be altered so as to optimise the level of expression obtained in the host cell. The host cell may be any appropriate prokaryotic or eukaryotic cell. For example, the host cell may be an E. coli cell or a human T cell. The alterations made to these genetic sequences are silent, that is they do not alter the amino acid sequence encoded. There are a number of companies which offer such expression optimisation services, including, GeneArt, Germany.

The invention also provides a method of producing a high affinity TCR having the property of binding to SLYNTVATL-HLA-A*0201. CHARACTERISED IN THAT the TCR (i) comprises at least one TCR α chain variable domain and/or at least one TCR β chain variable domain and (ii) has a $K_D$ for the said SLYNTVATL-HLA-A*0201 complex of less than or equal to 1 μM and/or an off-rate ($k_{off}$) for the SLYNTVATL-HLA-A*0201 complex of $1 \times 10^{-3}$ $S^{-1}$ or slower, wherein the method comprises:

(a) the production of a TCR comprising the α and β chain variable domains of the parental HIV Gag TCR wherein one or both of the α and β chain variable domains comprise a mutation(s) in one or more of the amino acids identified in claims 7 and 8;

(b) contacting said mutated TCR with SLYNTVATL-HLA-A*0201 under conditions suitable to allow the binding of the TCR to SLYNTVATL-HLA-A*0201;

and measuring the $K_D$ and/or $k_{off}$ of the interaction.

Preferred features of each aspect of the invention are as for each of the other aspects mutatis mutandis. The prior art documents mentioned herein are incorporated to the fullest extent permitted by law.

EXAMPLES

The invention is further described in the following examples, which do not limit the scope of the invention in any way.

Reference is made in the following to the accompanying drawings in which:

FIGS. 1a and 1b details the alpha chain variable domain amino acid and beta chain variable domain amino acid sequences of the parental HIV Gag TCR respectively.

FIGS. 2a and 2b show respectively the DNA sequence of soluble versions of the parental HIV Gag TCR α and β chains.

FIGS. 3a and 3b show respectively the HIV Gag TCR α and β chain extracellular amino acid sequences produced from the DNA sequences of FIGS. 2a and 2b.

FIGS. 4a and 4b show respectively the DNA sequence of soluble versions of the HIV Gag TCR α and β chains mutated to encode additional cysteine residues to form a non-native disulfide bond. The mutated codon is indicated by shading and The introduced restriction enzyme recognition sites are underlined.

FIGS. 5a and 5b show respectively the HIV Gag TCR α and β chain extracellular amino acid sequences produced from the DNA sequences of FIGS. 4a and 4b. The introduced cysteine in each chain is indicated by shading.

FIG. 6 details the alpha chain variable domain amino acid sequences of the high affinity HIV Gag TCR variants.

FIG. 7 details the beta chain variable domain amino acid sequences of the high affinity HIV Gag TCR variants.

FIG. 8a details the amino acid sequence of a soluble portion of TRAC.

FIG. 8b details the amino acid sequence of a soluble portion of TRBC1.

FIG. 8c details the amino acid sequence of a soluble portion of TRBC2.

FIG. 9 details the DNA sequence of the pEX954 plasmid.

FIG. 10 details the DNA sequence of the pEX821 plasmid.

FIG. 11 details the beta chain amino acid sequences of the parental soluble HIV Gag TCR variant fused via a peptide linker to wild-type human IL-2. The amino acids of the linker and IL-2 are indicated in italics.

FIG. 12 provides the Biacore response curves generated for the interaction of the soluble disulfide-linked parental HIV Gag TCR and the SLYNTVATL-HLA-A*0201 complex.

Figure 13:
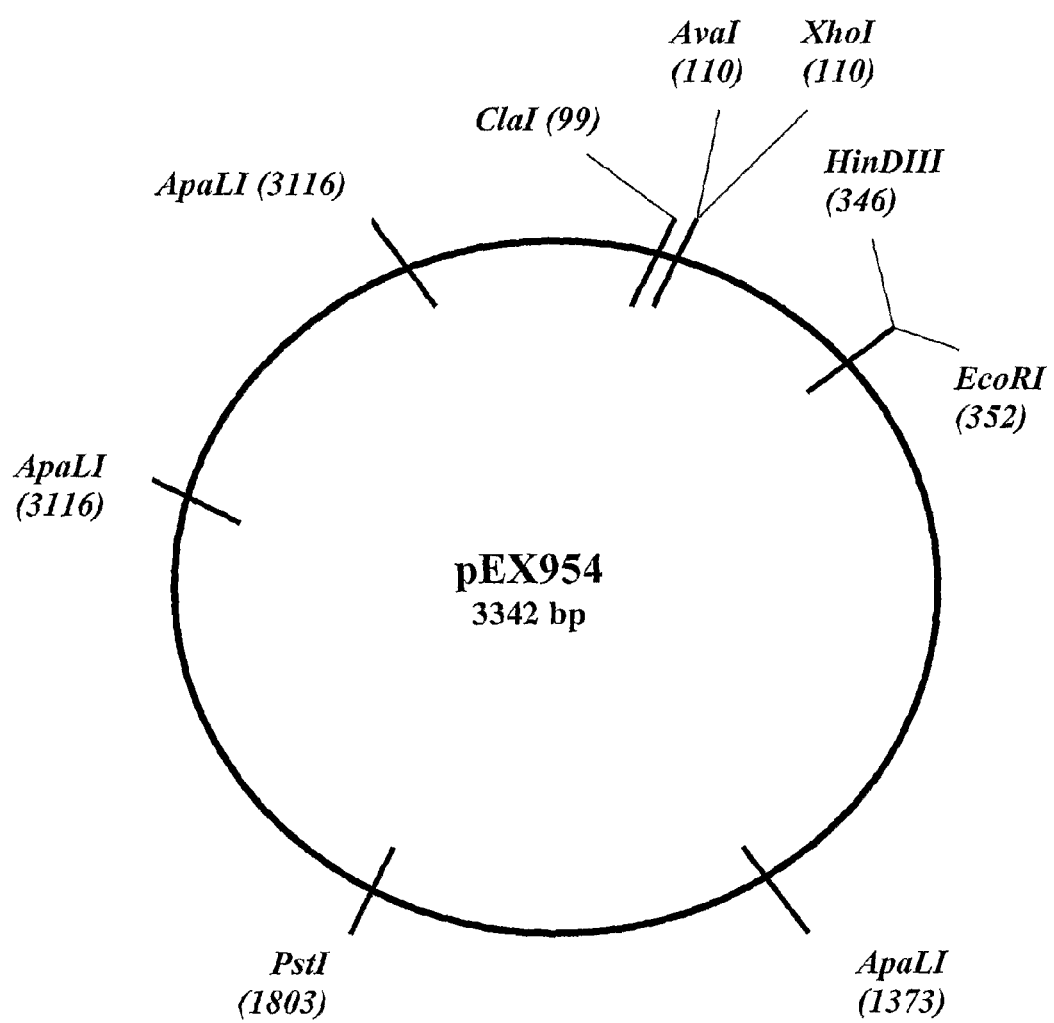

FIG. 13 provides a plasmid map of the pEX954 plasmid.

Figure 14:
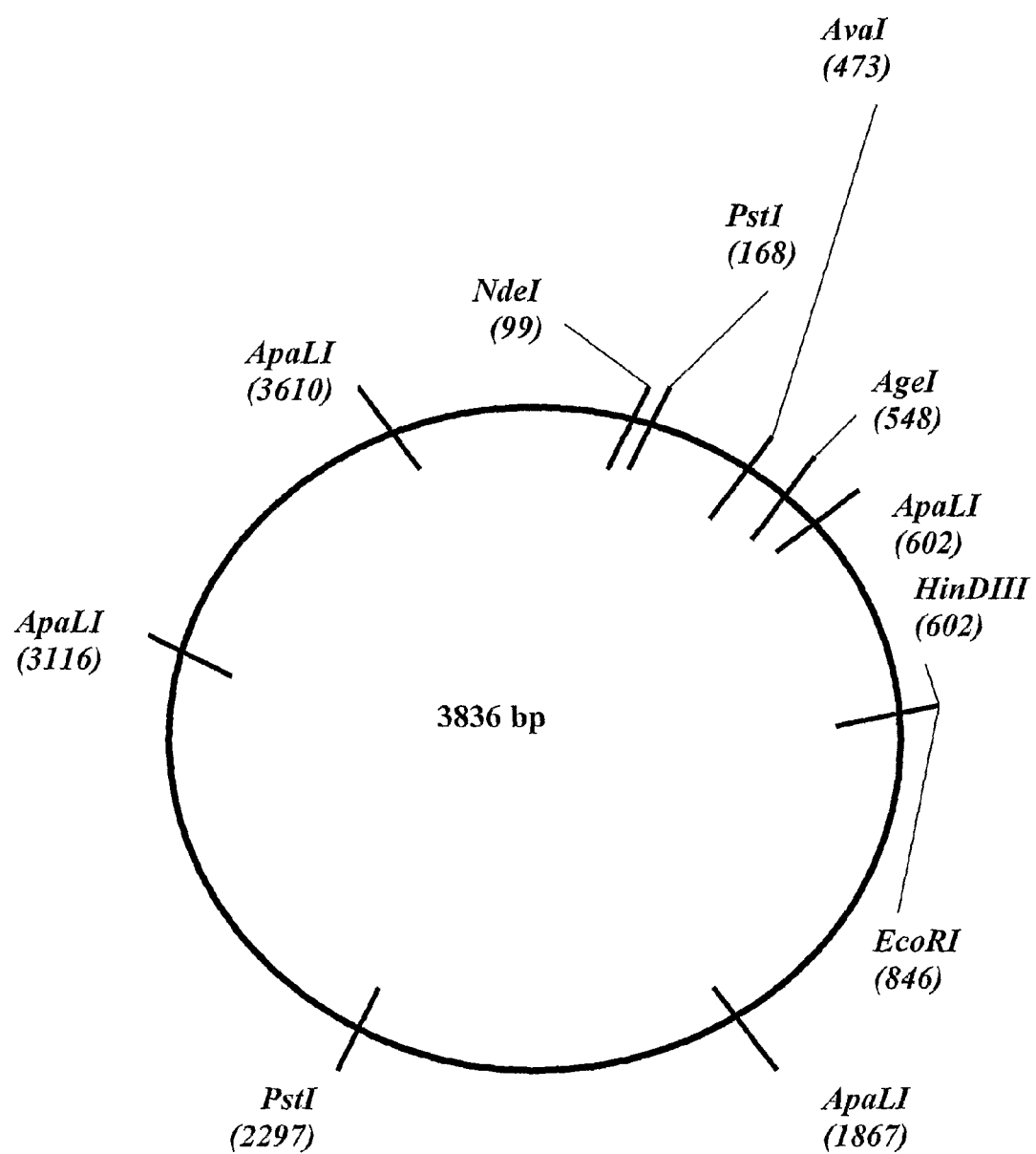

FIG. 14 provides a plasmid map of the pEX821 plasmid.

FIG. 15a provides the full-length DNA sequence of the parental HIV Gag TCR α chain optimised for expression in human T cells.

FIG. 15b provides the full-length DNA sequence of the parental HIV Gag TCR β chain optimised for expression in human T cells.

FIG. 16a provides the full-length amino acid sequence of the parental HIV Gag TCR α chain.

FIG. 16b provides the full-length amino acid sequence of the parental HIV Gag TCR β chain optimised for expression in human T cells.

Figure 17A:
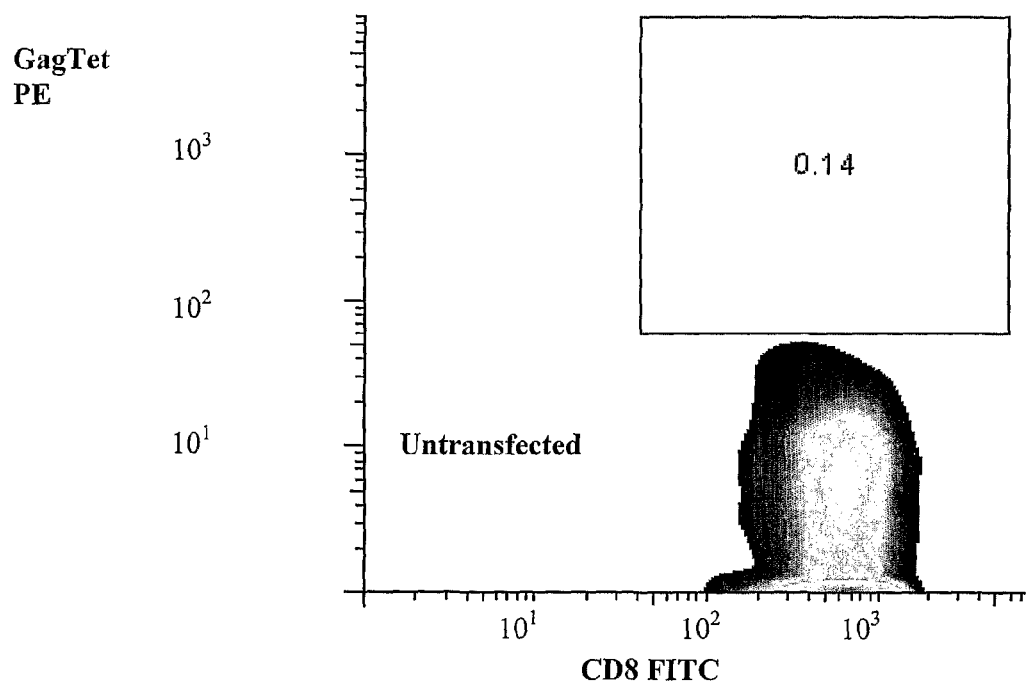

FIG. 17a provides FACS analysis data for untransduced control CD8+ T cells.

Figure 17B:
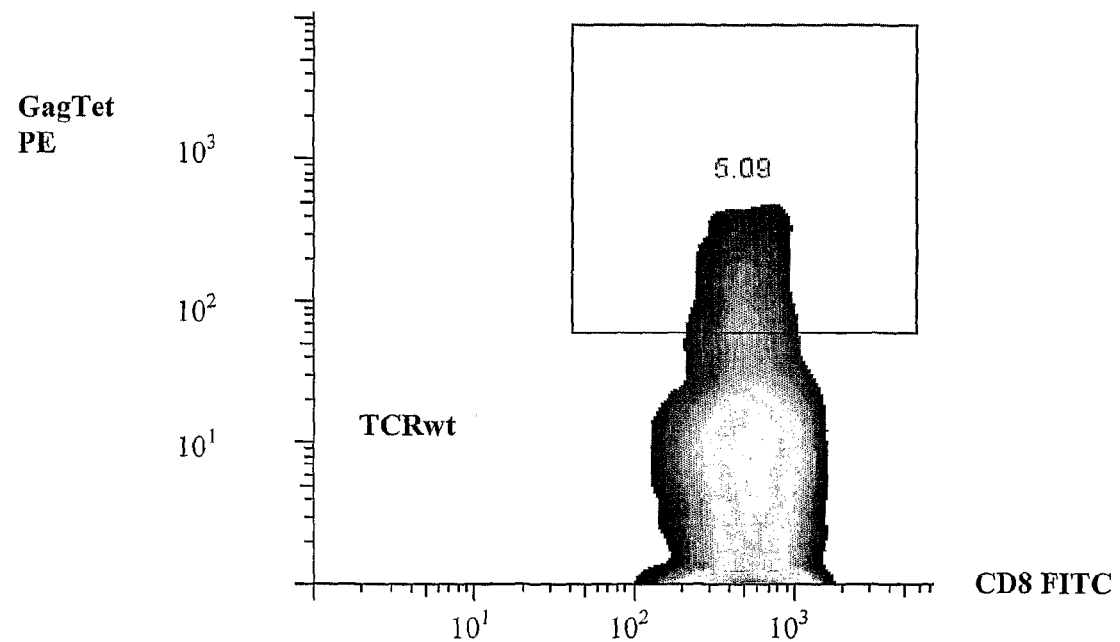

FIG. 17b provides FACS analysis data demonstrating expression of the parental HIV Gag TCR on the surface of transduced CD8+ T cells.

FIGS. 18a and 18b provide the amino acids sequences of the alpha and beta chains of a soluble disulfide-linked high affinity c11c6 HIV Gag TCR respectively.

Figure 19:
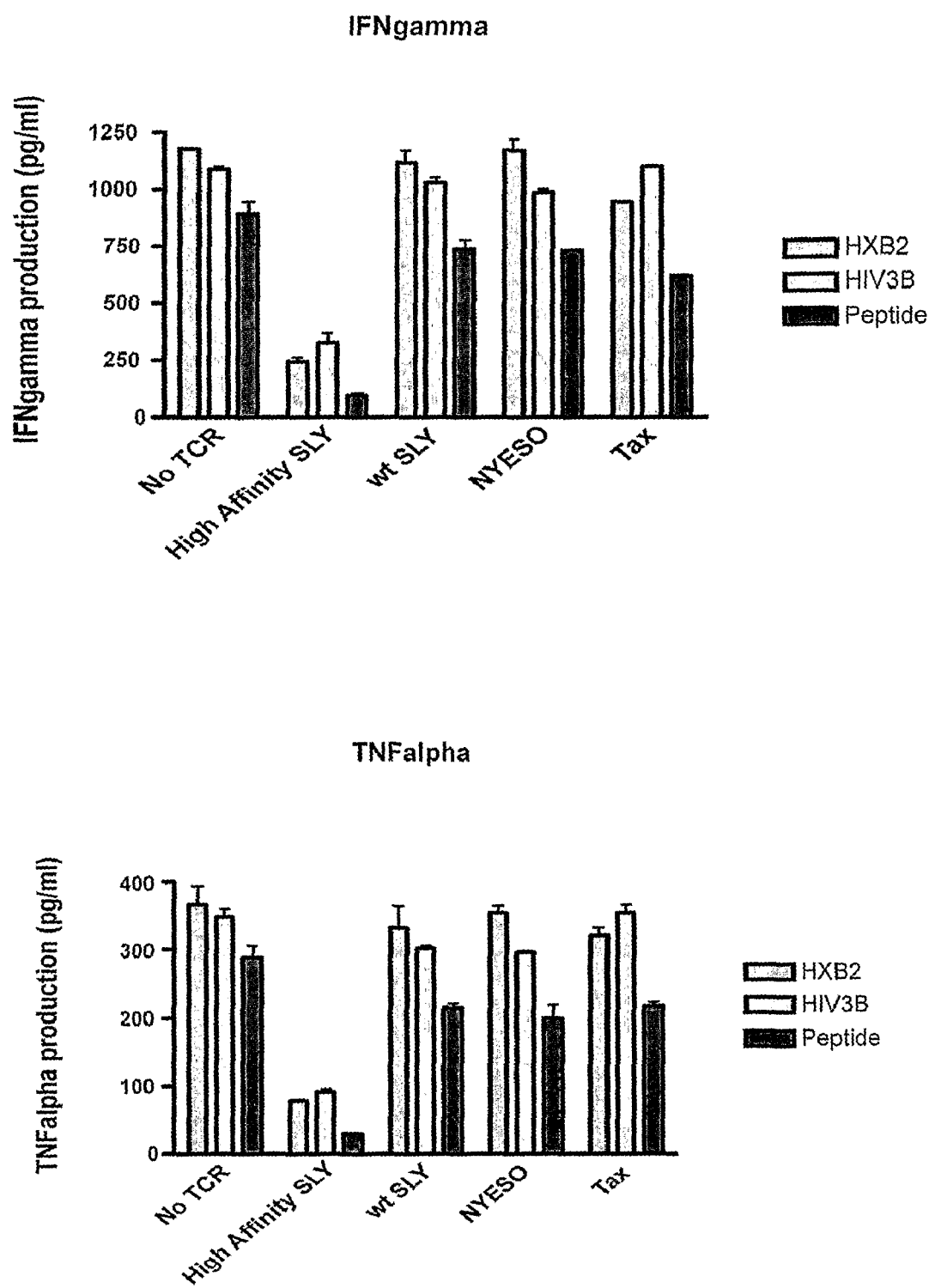

FIG. 19 demonstrates the ability of soluble disulfide-linked high affinity c11c6 HIV Gag TCRs to inhibit the activation of the SLYNTVATL-HLA-A*0201 reactive OX84 polyclonal T cell line in the presence of To cells infected with HIV as measured by IFN-γ and TNF-α production.

Figure 20:
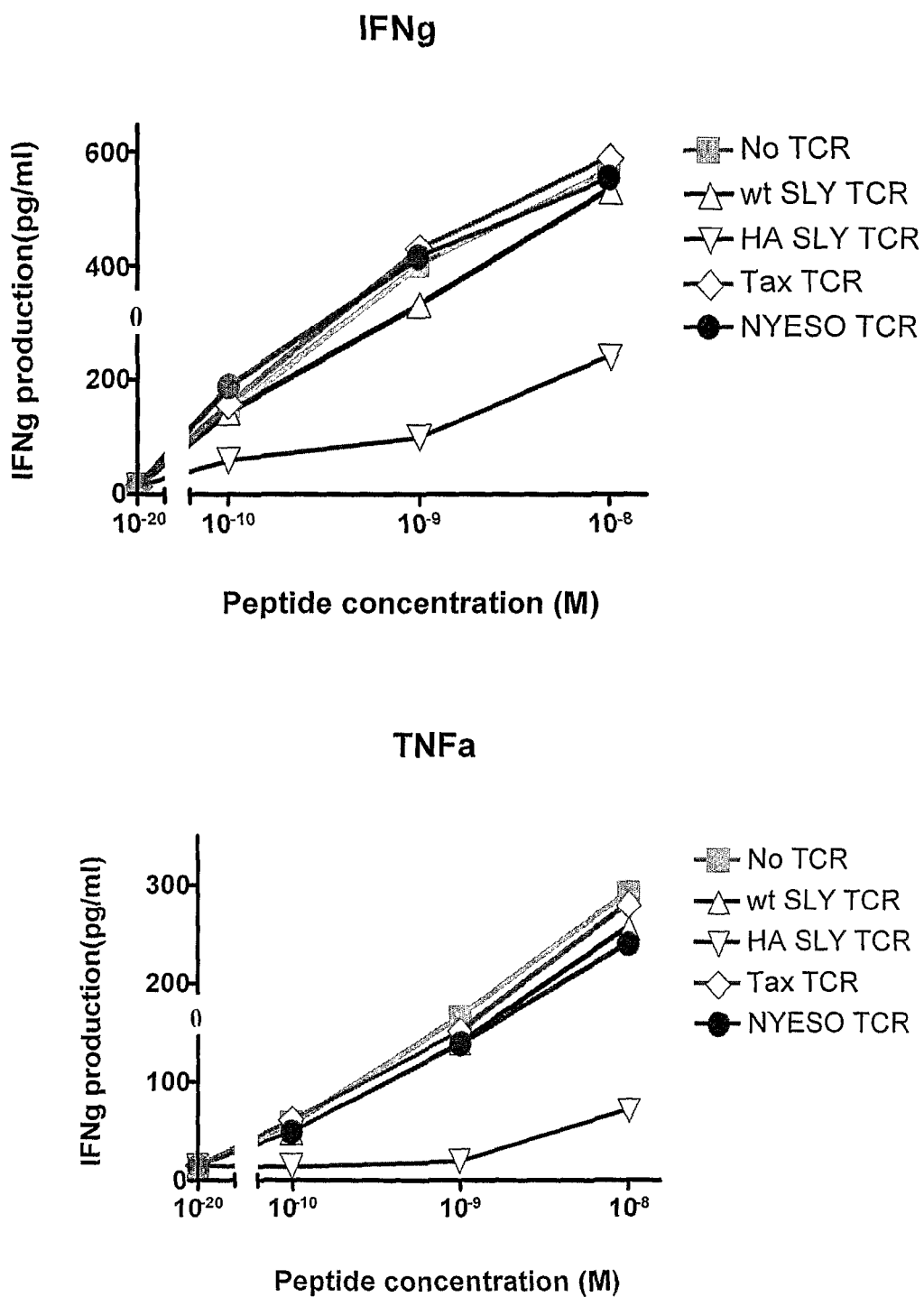

FIG. 20 demonstrates the ability of soluble disulfide-linked high affinity c 11c6 HIV Gag TCRs to inhibit the activation of the SLYNTVATL-HLA-A*0201 reactive OX84 polyclonal T cell line in the presence of SLYNTVATL peptide-pulsed uninfected To cells as measured by IFN-γ and TNF-α production.

Figure 21:
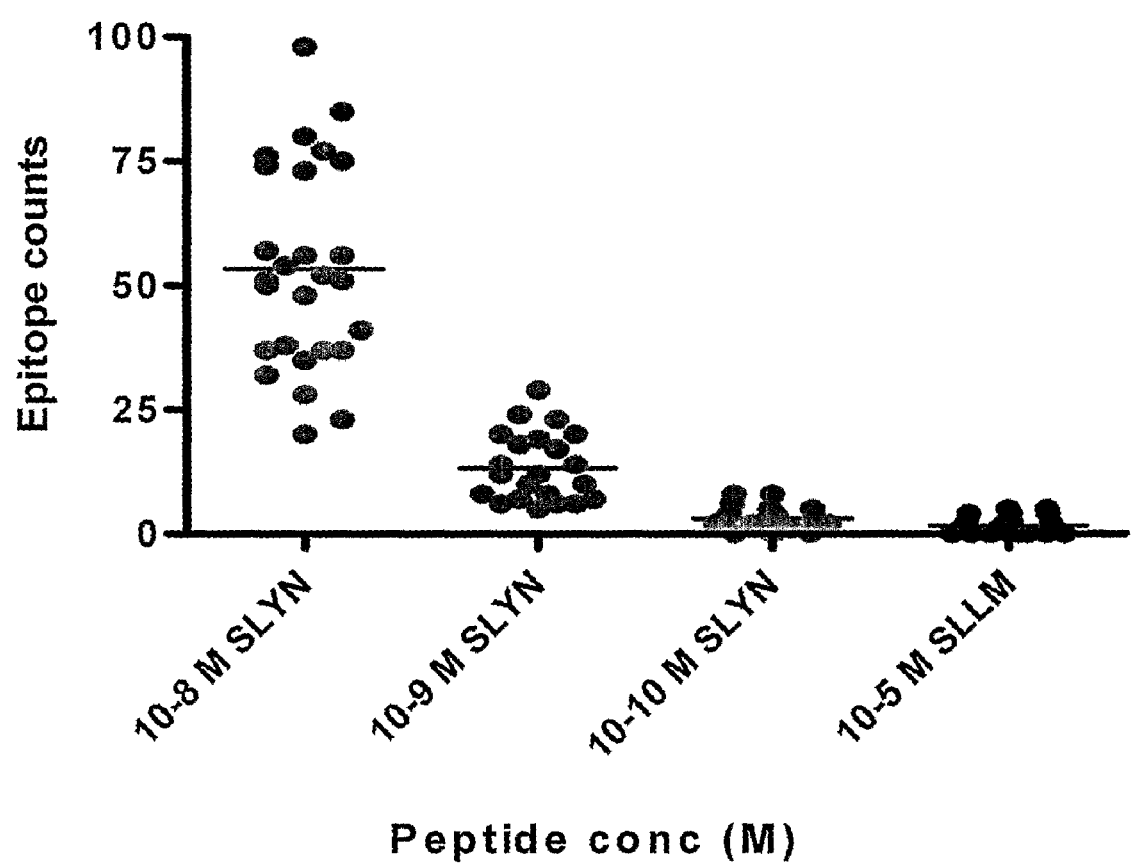

FIG. 21 demonstrates the ability of soluble disulfide-linked high affinity c 11c6 HIV Gag TCRs to stain SLYNTVATL peptide-pulsed T2 cells.

Example 1

Production of Soluble Disulfide-Linked TCRs Comprising the Parental HIV Gag TCR Variable Regions FIGS. 4a and 4b provide the DNA sequences of soluble disulfide-linked alpha beta chains from a parental TCR which is specific for the SLYNTVATL-HLA-A*0201 complex. These DNA sequences can be synthesis de-novo by a number of contract research companies, for example GeneArt (Germany). Restriction enzyme recognition sites are also added to these DNA sequences in order to facilitate ligation of these DNA sequences into the pGMT7-based expression plasmids, which contain the T7 promoter for high level expression in *E. coli* strain BL21-DE3(pLysS) (Pan et al., *Biotechniques* (2000) 29 (6): 1234-8)

The TCR alpha chain sequences contain introduced ClaI and SalII restriction enzyme recognition sites and this sequence was ligated into pEX954 (see FIGS. 9 and 13) cut with ClaI and XhoI.

The TCR beta chain sequences contain introduced AseI and AgeI restriction enzyme recognition sites and were ligated into pEX821 (see FIGS. 10 and 14) cut with NdeI/AgeI.

Restriction Enzyme Recognition Sites as Introduced into DNA Encoding the TCR Chains

| ClaI- | ATCGAT |
|---|---|
| SalII- | GTCGAC |
| AseI- | ATTAAT |
| AgeI- | ACCGGT |

Ligation

The cut TCR alpha and beta chain DNA and cut vector were ligated using a rapid DNA ligation kit (Roche) following the manufacturers instructions.

Ligated plasmids were transformed into competent *E. coli* strain XL1-blue cells and plated out on LB/agar plates containing 100 mg/ml ampicillin. Following incubation overnight at 37° C., single colonies were picked and grown in 10 ml LB containing 100 mg/ml ampicillin overnight at 37° C. with shaking. Cloned plasmids were purified using a Mini-prep kit (Qiagen) and the insert was sequenced using an automated DNA sequencer (Lark Technologies).

FIGS. 5*a* and 5*b* show respectively the soluble disulfide linked parental HIV gag TCR α and β chain extracellular amino acid sequences produced from the DNA sequences of FIGS. 4*a* and 4*b*

Example 2

Production of High Affinity Variants of the Soluble Disulfide Linked HIV Gag TCR The soluble disulfide-linked native HIV Gag TCR produced as described in Example 1 can be used a template from which to produce the TCRs of the invention which have an increased affinity for the SLYNTVATL (SEQ ID NO: 16)-HLA-A*0201 complex.

Phage display is one means by which libraries of HIV Gag TCR variants can be generated in order to identify high affinity mutants. For example, the TCR phage display and screening methods described in (Li et al., (2005) *Nature Biotech* 23 (3): 349-354) can be adapted and applied to HIV Gag TCRs.

The amino sequences of the mutated TCR alpha and beta chain variable domains which, when combined with an appropriate TCR chain, demonstrate high affinity for the SLYNTVATL-HLA-A*0201 complex, are listed in FIGS. 6 and 7 respectively. (SEQ ID Nos: 11-13 and 14-15 respectively) As is known to those skilled in the art the necessary codon changes required to produce these mutated chains can be introduced into the DNA encoding these chains by site-directed mutagenesis. (QuickChange™ Site-Directed Mutagenesis Kit from Stratagene)

Briefly, this is achieved by using primers that incorporate the desired codon change(s) and the plasmids containing the relevant TCR chain DNA as a template for the mutagenesis:

Mutagenesis was carried out using the following conditions: 50 ng plasmid template, 1 μl of 110 mM dNTP, 5 μl of 10× Pfu DNA polymerase buffer as supplied by the manufacturer, 25 pmol of fwd primer, 25 pmol of rev primer, 1 μl pfu DNA polymerase in total volume 50 μl. After an initial denaturation step of 2 mins at 95 C, the reaction was subjected to 25 cycles of denaturation (95 C, 10 secs), annealing (55 C 10 secs), and elongation (72 C, 8 mins). The resulting product was digested with DpnI restriction enzyme to remove the template plasmid and transformed into *E. coli* strain XL1-blue. Mutagenesis was verified by sequencing.

Example 3

Expression, Refolding and Purification of Soluble TCR

The expression plasmids containing the mutated α-chain and β-chain respectively as prepared in Examples 1 or 2 were transformed separately into *E. coli* strain BL21pLysS, and single ampicillin-resistant colonies were grown at 37° C. in TYP (ampicillin 100 μg/ml) medium to $OD_{600}$ of 0.4 before inducing protein expression with 0.5 mM IPTG. Cells were harvested three hours post-induction by centrifugation for 30 minutes at 4000 rpm in a Beckman J-6B. Cell pellets were re-suspended in a buffer containing 50 mM Tris-HCl, 25% (w/v) sucrose, 1 mM NaEDTA, 0.1% (w/v) NaAzide, 10 mM DTT, pH 8.0. After an overnight freeze-thaw step, re-suspended cells were sonicated in 1 minute bursts for a total of around 10 minutes in a Milsonix XL2020 sonicator using a standard 12 mm diameter probe. Inclusion body pellets were recovered by centrifuigation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl, 0.5% Triton-X100, 200 mM NaCl, 10 mM NaEDTA, 0.1% (w/v) NaAzide, 2 mM DTT, pH 8.0) before being pelleted by centrifugation for 15 minutes at 1300 rpm in a Beckman J2-21. Detergent and salt was then removed by a similar wash in the following buffer: 50 mM Tris-HCl, 1 mM NaEDTA, 0.1% (w/v) NaAzide, 2 mM DTT, pH 8.0. Finally, the inclusion bodies were divided into 30 mg aliquots and frozen at −70° C. Inclusion body protein yield was quantitated by solubilising with 6M guanidine-HCl and measurement with a Bradford dye-binding assay (PerBio).

Approximately 30 mg of TCR β chain and 60 mg of TCR α chain solubilised inclusion bodies were thawed from frozen stocks, samples were then mixed and the mixture diluted into 15 ml of a guanidine solution (6 M Guanidine-hydrochloride, 10 mM Sodium Acetate, 10 mM EDTA), to ensure complete chain de-naturation. The guanidine solution containing fully reduced and denatured TCR chains was then injected into 1 liter of the following refolding buffer: 100 mM Tris pH 8.5, 400 mM L-Arginine, 2 mM EDTA, 5 mM reduced Glutathione, 0.5 mM oxidised Glutathione, 5M urea, 0.2 mM PMSF. The redox couple (2-mercaptoethylamine and cystamine (to final concentrations of 6.6 mM and 3.7 mM, respectively) were added approximately 5 minutes before addition of the denatured TCR chains. The solution was left for 5 hrs±15 minutes. The refolded TCR was dialysed in Spectrapor 1 membrane (Spectrum; Product No. 132670) against 10 L 10 mM Tris pH 8.1 at 5° C.±3° C. for 18-20 hours. After this time, the dialysis buffer was changed to fresh 10 mM Tris pH 8.1 (10 L) and dialysis was continued at 5° C.±3° C. for another 20-22 hours.

sTCR was separated from degradation products and impurities by loading the dialysed refold onto a POROS 50HQ anion exchange column and eluting bound protein with a gradient of 0-500 mM NaCl over 50 column volumes using an Akta purifier (Pharmacia). Peak fractions were stored at 4° C. and analysed by Coomassie-stained SDS-PAGE before being pooled and concentrated. Finally, the sTCR was purified and characterised using a Superdex 200HR gel filtration column pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa was pooled and concentrated prior to characterisation by BIAcore surface plasmon resonance analysis.

Example 4

Biacore Surface Plasmon Resonance Characterisation of sTCR Binding to Specific pMHC A surface plasmon resonance biosensor (Biacore 3000™) was used to analyse the binding of a sTCR to its peptide-MHC ligand. This was facilitated by producing single pMHC complexes (described below) which were immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class 1 molecules to be manipulated easily.

Biotinylated class I HLA-A*0201 molecules were refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15). HLA-A*0201-heavy chain was expressed with a C-terminal biotinylation tag which replaces the transmembrane and cytoplasmic domains of the protein in an appropriate construct. Inclusion body expression levels of ~75 mg/liter bacterial culture were obtained. The MHC light-chain or β2-microglobulin was also expressed as inclusion bodies in *E. coli* from an appropriate construct, at a level of 500 mg/liter bacterial culture.

*E. coli* cells were lysed and inclusion bodies are purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/liter heavy chain, 30 mg/liter β2m into 0.4 M L-Arginine-HCl, 100 mM Tris pH 8.1, 3.7 mM cystamine, 6.6 mM β-cysteamine, 4 mg/ml of the SLYNTVATL peptide required to be loaded by the HLA-A*0201 molecule, by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 μm cellulose acetate filter and loaded onto a POROS 50HQ anion exchange column (8 ml bed volume). Protein was eluted with a linear 0-500 mM NaCl gradient. HLA-A*0201-peptide complex eluted at approximately 250 mM NaCl, and peak fractions were collected, a cocktail of protease inhibitors (Calbiochem) was added and the fractions were chilled on ice.

Biotinylation tagged pMHC molecules were buffer exchanged into 10 mM Tris pH 8.1, 5 mM NaCl using a Pharmacia fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl2, and 5 μg/ml BirA enzyme (purified according to O'Callaghan et al. (1999) *Anal. Biochem.* 266: 9-15). The mixture was then allowed to incubate at room temperature overnight.

The biotinylated pHLA-A*0201 molecules were purified using gel filtration chromatography. A Pharmacia Superdex 75 HR 10/30 column was pre-equilibrated with filtered PBS and 1 ml of the biotinylation reaction mixture was loaded and the column was developed with PBS at 0.5 ml/min. Biotinylated pHLA-A*0201 molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pHLA-A*0201 molecules were stored frozen at −20° C. Streptavidin was immobilised by standard amine coupling methods.

Such immobilised complexes are capable of binding both T-cell receptors and the coreceptor CD8αα, both of which may be injected in the soluble phase. Specific binding of TCR is obtained even at low concentrations (at least 40 μg/ml), implying the TCR is relatively stable. The pMHC binding properties of sTCR are observed to be qualitatively and quantitatively similar if sTCR is used either in the soluble or immobilised phase. This is an important control for partial activity of soluble species and also suggests that biotinylated pMHC complexes are biologically as active as non-biotinylated complexes.

The interactions between HIV Gag sTCR containing a novel inter-chain bond and its ligand/MHC complex or an irrelevant HLA-peptide combination, the production of which is described above, were analysed on a Biacore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the individual HLA-peptide complexes in separate flow cells via binding between the biotin cross linked onto β2m and streptavidin which have been chemically cross linked to the activated surface of the flow cells. The assay was then performed by passing sTCR over the surfaces of the different flow cells at a constant flow rate, measuring the SPR response in doing so.

To Measure Equilibrium Binding Constant

Serial dilutions of the parental or mutated HIV Gag sTCR were prepared and injected at constant flow rate of 5 μl min-1 over two different flow cells; one coated with ~1000 RU of specific SLYNTVATL-HLA-A*0201 complex, the second coated with ~1000 RU of non-specific HLA-A2-peptide complex. Response was normalised for each concentration using the measurement from the control cell. Normalised data response was plotted versus concentration of TCR sample and fitted to a hyperbola in order to calculate the equilibrium binding constant, $K_D$. (Price & Dwek, Principles and Problems in Physical Chemistry for Biochemists ($2^{nd}$ Edition) 1979, Clarendon Press, Oxford).

19

To measure Kinetic Parameters

For high affinity TCRs $K_D$ was determined by experimentally measuring the dissociation rate constant, kd, and the association rate constant, ka. The equilibrium constant $K_D$ was calculated as kd/ka.

TCR was injected over two different cells one coated with ~300 RU of specific HLA-A2-nyeso peptide complex, the second coated with ~300 RU of non-specific HLA-A2-peptide complex. Flow rate was set at 50 μl/min. Typically 250 μl of TCR at ~3 μM concentration was injected. Buffer was then flowed over until the response had returned to baseline. Kinetic parameters were calculated using Biaevaluation software, The dissociation phase was also fitted to a single exponential decay equation enabling calculation of half-life.

Results

The interaction between a soluble disulfide-linked native HIV Gag TCR (consisting of the α and β TCR chains detailed in SEQ ID NOs 9 and 10 respectively) and the SLYNTVATL-HLA-A*0201 complex was analysed using the above methods and demonstrated a $K_D$ of 85 nM and an off-rate ($k_{off}$) of $2.21 \times 10^{-2}$ S$^{-1}$. (See FIG. 12 for Biacore response curves)

The TCRs specified in the following table have a $K_D$ of less than or equal to 1 μM and/or a $k_{off}$ of $1 \times 10^{-3}$ S$^{-1}$ or slower.

| Alpha chain variable domain sequence, SEQ ID NO: | Beta chain variable domain sequence, SEQ ID NO: |
|---|---|
| 1 | 2 |
| 1 | 14 |
| 1 | 15 |
| 11 | 2 |
| 12 | 2 |
| 13 | 2 |
| 12 | 15 |
| 13 | 15 |
| 12 | 14 |
| 13 | 14 |

Example 5

Production of a Soluble High Affinity HIV Gag TCR-WT Human IL-2 Fusion Protein

The methods substantially as described in Examples 1 to 3 can be used to produce a soluble high affinity HIV Gag TCR-WT human IL-2 fusion protein. Briefly, the DNA encoding the desired linker and WT human IL-2 are added into the 3' end of the DNA sequence of the soluble disulfide-linked parental HIV Gag TCR beta chain immediately prior to the TAA ("Stop") codon. FIG. 11 provides the amino acid sequence of a fusion protein comprising a disulfide-linked parental HIV Gag TCR beta chain fused to WT human IL-2 via linker sequence. (SEQ ID NO: 24) The linker and IL-2 portion of this fusion protein are indicated in italics. The DNA encoding this construct can then be ligated into pEX821. The soluble parental HIV Gag TCR-IL-2 fusion protein can then be expressed by combining this beta chain fusion protein with the soluble disulfide-linked parental HIV Gag alpha chain TCR chain detailed in FIG. 5a (SEQ ID NO: 9) using the methods substantially as described in Example 3.

Example 6

Recombinant Expression of the Parental HIV Gag TCR on the Surface of T Cells

DNA constructs encoding the signal sequence, extracellular, transmembrane and intracellular domains of the parental

20

HIV Gag TCR chains were synthesised (GeneArt, Germany). These TCR α chain and TCR β chain DNA sequences, provided in FIGS. 15a and 15b respectively, are altered from the parental HIV Gag TCR DNA sequences so as to enhance expression levels of the encoded TCR chains in human T cells whilst maintaining the native amino acid sequence. FIGS. 16a and 16b provide the full-length amino acid sequences encoded by the DNA sequences of FIGS. 15a and 15b respectively.

TCR α chain and TCR β chain DNA sequences were then inserted together into a Lentiviral expression vector. This vector contains DNA encoding both the parental HIV Gag TCR α chain and β chain as a single open reading frame with the in-frame Foot and Mouth Disease Virus (FMDV) 2A cleavage factor amino acid sequence (LLNFDLLKLAGD-VESNPG (SEQ ID NO: 31)) separating the TCR chains. (de Felipe et al., *Genet Vaccines Ther* (2004) 2 (1): 13) On mRNA translation the TCR α chain is produced with the 2A peptide sequence at its C-terminus and the TCR β chain is produced as a separate polypeptide.

T cells were transduced with the above Lentiviral vector. Briefly, primary T cells were stimulated for 24 hours using anti-CD3/anti-CD28 beads. A concentrated Lentivirus supernatant, expressing the TCR genes, was then incubated with the stimulated T cells to allow viral transduction. The anti-CD3/anti-CD28 beads were then removed and the transduced T cells were cultured until they attained a "resting volume" of 200-300 fL.

Presentation of parental HIV Gag TCRs on the surface of the transduced cells was confirmed by FACS analysis using HLA-A*0201-SLYNTVALT PE tetramer and anti-CD8 monoclonal antibody FITC co-staining.

Results

FIG. 17b provides the FACS analysis data which demonstrates the successful expression of the parental HIV Gag TCR on the surface of transduced CD8+ T cells. FIG. 17a provides FACS analysis data generated using control untransduced T cells.

Example 7

Inhibition of CTL Activation by Soluble High Affinity HIV Gag TCRs

The following assays were carried out to demonstrate that the soluble high affinity c11c6 HIV Gag TCR was capable of inhibiting activation of a SLYNTVATL-HLA-A*0201 reactive polyclonal T cell line.

Inhibition of Activation of the OX84 SLYNTVATL-HLA-A*0201 Reactive Polyclonal T Cell Line in the of Presence of HIV Infected Cells The soluble c11c6 high affinity HIV Gag TCR utilised in this experiment contained the TCR alpha chain variable domain and TCR beta chain variable regions shown in FIG. 6c (SEQ ID NO: 13) and FIG. 7b (SEQ ID NO: 15) respectively. The full amino acid sequences of the TCR alpha and beta chains of this soluble TCR are provided by FIG. 18a (SEQ ID NO: 29) and FIG. 18b (SEQ ID NO: 30) respectively.

IFN-γ and TNF-α production was used as the read-outs for CTL activation.

Reagents

R10 Assay media: 10% FCS (heat-inactivated, Gibco, cat #10108-165), 88% RPMI 1640 (Gibco, cat #42401-018), 1% glutamine (Gibco, cat #25030-024) and 1% penicillin/streptomycin (Gibco, cat #15070-063).

Peptide: (obtained from various sources) initially dissolved in DMSO (Sigma, cat #D2650) at 4 mg/ml and frozen.

The BD™ Cytometric Bead Array Kit, Human Th1/Th2 cytokine Kit II (BD Biosciences, San Diego, US) contains all the reagents required for the assay.

T Cell Activation Assay

Chronically HIV infected To target cells (HXB2 and HIV3B HIV Lab strains) were washed and re-suspended in R10 media. As a control uninfected To target cells were pulsed with 1 nM of SLYNTVATL peptide, for 30 minutes at 37° C., 5% $CO_2$.

Test Samples:

25,000 HIV infected To target cells in R10 media per well of a 96 well U-bottom plate.

$2 \times 10^{-7}$ M high affinity cl c6 HIV Gag TCR or parental HIV Gag TCR in R10 media per well.

5000 OX84 polyclonal effector T cell line in R10 media per well.

Controls:

As above substituting irrelevant soluble TCRs (HLA-A*0201-Tax specific and HLA-A*0201-NY-ESO specific TCRs) or the high affinity HIV Gag TCRs.

The plate was then incubated for 4 hours at 37° C., 5% $CO_2$. The culture supernatant was removed to measure the levels of IFN-γ and TNF-α present using the following method.

IFN-γ and TNF-α Assay

BD™ Cytometric Beads coated with (a) anti-IFNγ capture antibodies and (b) anti-TNFα capture antibodies were prepared according to the manufacturers instructions A number of assay tubes were then prepared containing the following additions:

50 μl of mixed anti-IFNγ and anti-TNFα BD™ Cytometric Beads in BD Assay Diluent

50 μl of PE Detection Reagent

Followed by either:

50 μl of the culture supernatant taken from the T cell activation assay wells. (Test Samples)

Or

50 μl of mixed IFNγ and TNFα standards prepared at a range of concentrations by serial dilution of stock standards. (Calibration Standards)

The tube were then incubated in the dark for 3 hours prior to being washed with 1 ml of BD Wash Buffer and centrifuged. Finally, the beads were re-suspended in 300 μl of the Wash Buffer and the level of IFNγ and TNFα present was determined by Flow Cytometry according to manufacturer's instructions.

Inhibition of the SLYNTVATL-HLA-A*0201 Specific OX84 Polyclonal T Line in the Presence of Uninfected SLYNTVATL Peptide Pulsed to Cells The same regents and methods as used for the above CTL activation assay were used except that:

2000 OX84 polyclonal effector T cells were used in each T cell activation assay.

Uninfected To lymphoblastoid cells, pulsed with $10^{-10}$–$10^{-8}$ M SLYNTVATL peptide were used as the target cells Results The soluble high affinity c 11c6 HIV Gag TCR strongly inhibited activation of the SLYNTVATL-HLA-A*0201 reactive OX84 polyclonal T cell line in the presence of To cells infected by HIV as measured by IFN-γ and TNF-α production. (See FIG. 19)

The soluble high affinity c11c6 HIV Gag TCR strongly inhibited activation of the SLYNTVATL-HLA-A*0201 reactive OX84 polyclonal T cell line in the presence of SLYNTVATL-pulsed uninfected To cells as measured by IFN-γ and TNF-α production. (See FIG. 20)

Example 8

Quantification of Cell Surface SLYNTVATL-HLA-A*0201 Antigens on Peptide-Pulsed T2 Cells by Fluorescence Microscopy Using High Affinity c11c6 HIV Gag TCR The number of SLYNTVATL-HLA-A*0201 antigens on peptide-pulsed T2 lymphoblastoid cell was determined (on the assumption that one fluorescence signal relates to a single labelled TCR bound to its cognate pMHC ligand on the surface of the target cell) by single molecule fluorescence microscopy using a soluble high-affinity c11c6 HIV Gag TCR. This was facilitated by using biotinylated TCR to target the antigen-expressing cancer cells and subsequent labelling of cell-bound TCR by streptavidin-R phycoerythrin (PE) conjugates. Individual PE molecules were then imaged by 3-dimensional fluorescence microscopy.

T2 lymphoblastoid cells were pulsed with the HIV Gag-derived SLYNTVATL peptide, or an irrelevant peptide (SLLMWITQC) at a range of concentrations ($10^{-5}$–$10^{-10}$M) for 90 minutes at 37° C. After pulsing the cells were washed twice with 500 μl of PBS. Cells were incubated in 200 μl of TCR solution (100 nM high-affinity c11c6 HIV Gag TCR), in PBS. 0.5% BSA albumin) for 30 min at room temperature. TCR solution was removed, and cells were washed three times with 500 μl of PBS. Cells were incubated in 200 μl of streptavidin-PE solution (5 μg ml$^{-1}$ streptavidin-PE in PBS containing 0.5% BSA) at room temperature in the dark for 20 min. Streptavidin-PE solution was removed and cells were washed three times with 500 μl of PBS. Wash media was removed, and cells kept in 400 μl of R10, without Phenol Red before imaging by fluorescence microscopy.

Fluorescence microscopy. Fluorescent microscopy was carried out using an Axiovert 200M (Zeiss) microscope with a 63× Oil objective (Zeiss). A Lambda LS light source containing a 300 W Xenon Arc lamp (Sutter) was used for illumination, and light intensity was reduced to optimal levels by placing a 0.3 and a 0.6 neutral density filter into the light path. Excitation and emission spectra were separated using a TRITC/DiI filter set (Chroma). Cells were imaged in three dimensions by z-stack acquisition (21 planes, 1 μm apart). Image acquisition and analysis was performed using Metamorph software (Universal Imaging) as described (Irvine et al., *Nature* 419: p 845-9, and Purbhoo et al., Nature Immunology 5: p 524-30).

Results

As shown by FIG. 21 the above method was used successfully to image high affinity c11c6 HIV Gag TCR bound to SLYNTVATL-HLA-A*0201 antigens on the surface of peptide-pulsed T2 cells. These results show the threshold for counting epitopes on SLYNTVATL peptide-pulsed cells using the high affinity c6c11 HIV Gag TCR is approximately $10^{-9}$ M peptide.

The invention claimed is:

1. An isolated or recombinant T-cell receptor (TCR) comprising an α chain variable domain and a β chain variable domain wherein:
the TCR binds to SLYNTVATL (SEQ ID NO:16)-HLA-A*0201 with a $K_D$ of less than or equal to 1 μM, and
the α chain variable domain comprises SEQ ID NO:1, and
the β chain variable domain comprises SEQ ID NO:2.

2. An isolated or recombinant T-cell receptor (TCR) comprising an α chain variable domain and a β chain variable domain wherein:
the TCR binds to SLYNTVATL (SEQ ID NO:16)-HLA-A*0201 with a $K_D$ of less than or equal to 1 μM and/or an off-rate ($k_{off}$) of $1 \times 10^{-3}$ $S^{-1}$ or slower using Surface Plasmon Resonance, and
the α chain variable domain comprises SEQ ID NO:1 with at least one mutation in at least one complementarity determining region selected from the group consisting of at least one of 95T, 96N, 97S, 98G and 100A, or
the β chain variable domain comprises SEQ ID NO:2 with at least one mutation in at least one complementarity determining region selected from the group consisting of at least one of 51Y, 52E, 53E and 54E wherein:
if the α chain variable domain is mutated, the β chain variable domain comprises SEQ ID NO:2, and if the β chain variable domain is mutated, the α chain variable domain comprises SEQ ID NO:1.

3. An isolated or recombinant T-cell receptor (TCR) comprising an α chain variable domain and a β chain variable domain wherein:
the TCR binds to SLYNTVATL (SEQ ID NO:16)-HLA-A*0201 with a $K_D$ of less than or equal to 1 μM and/or an off-rate ($k_{off}$) of $1 \times 10^{-3}$ $S^{-1}$ or slower using Surface Plasmon Resonance, and
the α chain variable domain comprises SEQ ID NO:1 with at least one mutation in at least one complementarity determining region selected from the group consisting of, 95T, 96N, 97S, 98G and 100A, and
the β chain variable domain comprises SEQ ID NO:2 with at least one mutation in at least one complementarity determining region selected from the group consisting of, 51Y, 52E, 53E and 54E.

4. The TCR of claim 3 wherein the TCR comprises the α chain variable domain wherein all of 95T, 96N, 97S, 98G and 100A are mutated, and the β chain variable domain wherein all of 51Y, 52E, 53E or 54E are mutated.

5. An isolated or recombinant T-cell receptor (TCR) comprising an α chain variable domain and a β chain variable domain wherein:
the TCR binds to SLYNTVATL (SEQ ID NO:16)-HLA-A*0201 with a $K_D$ of less than or equal to 1 μM and/or an off-rate ($k_{off}$) of $1 \times 10^{-3}$ $S^{-1}$ or slower using Surface Plasmon Resonance, and
the α chain variable domain comprises SEQ ID NO:1 with one or more of amino acids 95S, 95G, 96A, 97H, 98D or 100S, and is hence mutated relative to SEQ ID NO:1, and
the β chain variable domain comprises SEQ ID NO:2 with one or more of amino acids 51V, 51A, 52R, 52L, 53G or 54V, and is hence mutated relative to SEQ ID NO:2.

6. The TCR of claim 5 wherein α chain variable domain comprises amino acids 95S, 95G, 96A, 97H, 98D and 100S, mutated relative to SEQ ID NO:1; and the β chain variable domain comprises amino acids 51V, 51A, 52R, 52L, 53G and 54V, mutated relative to SEQ ID NO:2.

7. An isolated or recombinant T-cell receptor (TCR) comprising an α chain variable domain and a β chain variable domain wherein:
the TCR binds to SLYNTVATL (SEQ ID NO:16)-HLA-A*0201 with a $K_D$ of less than or equal to 1 μM and/or an off-rate ($k_{off}$) of $1 \times 10^{-3}$ $S^1$ or slower using Surface Plasmon Resonance, and
the α chain variable domain comprises the amino acid sequence shown in any one of SEQ ID NOS:11-13, and
the β chain variable domain comprises the amino acid sequence shown in any one of SEQ ID NOS:14-15.

8. An isolated or recombinant T-cell receptor (TCR) comprising an α chain variable domain and a β chain variable domain wherein:
the TCR binds to SLYNTVATL (SEQ ID NO:16)-HLA-A*0201 with a $K_D$ of less than or equal to 1 μM and/or an off-rate ($k_{off}$) of $1 \times 10^{-3}$ $S^{-1}$ or slower using Surface Plasmon Resonance, and the α chain variable domain comprises the amino acid sequence shown in SEQ ID NO:1 and the β chain variable domain comprises the amino acid sequence shown in SEQ ID NO:14; or the α chain variable domain comprises the amino acid sequence shown in SEQ ID NO:1 and the β chain variable domain comprises the amino acid sequence shown in SEQ ID NO:15; or the α chain variable domain comprises the amino acid sequence shown in SEQ ID NO:11 and the β chain variable domain comprises the amino acid sequence shown in SEQ ID NO:2; or the α chain variable domain comprises the amino acid sequence shown in SEQ ID NO:12 and the β chain variable domain comprises the amino acid sequence shown in SEQ ID NO:2; or the α chain variable domain comprises the amino acid sequence shown in SEQ ID NO:13 and the β chain variable domain comprises the amino acid sequence shown in SEQ ID NO:2; or the α chain variable domain comprises the amino acid sequence shown in SEQ ID NO:12 and the β chain variable domain comprises the amino acid sequence shown in SEQ ID NO:15; or the α chain variable domain comprises the amino acid sequence shown in SEQ ID NO:13 and the β chain variable domain comprises the amino acid sequence shown in SEQ ID NO:15; or the α chain variable domain comprises the amino acid sequence shown in SEQ ID NO:12 and the β chain variable domain comprises the amino acid sequence shown in SEQ ID NO:14; or the α chain variable domain comprises the amino acid sequence shown in SEQ ID NO:13 and the β chain variable domain comprises the amino acid sequence shown in SEQ ID NO:14.

9. The TCR of claim 8 wherein the α chain variable domain comprises the amino acid sequence shown in SEQ ID NO:1 and the β chain variable domain comprises the amino acid sequence shown in SEQ ID NO:14.

10. The TCR of claim 8 wherein the α chain variable domain comprises the amino acid sequence shown in SEQ ID NO:1 and the β chain variable domain comprises the amino acid sequence shown in SEQ ID NO:15.

11. The TCR of claim 8 wherein the α chain variable domain comprises the amino acid sequence shown in SEQ ID NO:11 and the β chain variable domain comprises the amino acid sequence shown in SEQ ID NO:2.

12. The TCR of claim 8 wherein the α chain variable domain comprises the amino acid sequence shown in SEQ ID NO:12 and the β chain variable domain comprises the amino acid sequence shown in SEQ ID NO:2.

13. The TCR of claim 8 wherein the α chain variable domain comprises the amino acid sequence shown in SEQ ID NO:13 and the β chain variable domain comprises the amino acid sequence shown in SEQ ID NO:2.

14. The TCR of claim 8 wherein the α chain variable domain comprises the amino acid sequence shown in SEQ ID NO:12 and the β chain variable domain comprises the amino acid sequence shown in SEQ ID NO:15.

15. The TCR of claim 8 wherein the α chain variable domain comprises the amino acid sequence shown in SEQ ID NO:13 and the β chain variable domain comprises the amino acid sequence shown in SEQ ID NO:15.

16. The TCR of claim 8 wherein the α chain variable domain comprises the amino acid sequence shown in SEQ ID NO:12 and the β chain variable domain comprises the amino acid sequence shown in SEQ ID NO:14.

17. The TCR of claim 8 wherein the α chain variable domain comprises the amino acid sequence shown in SEQ ID NO:13 and the β chain variable domain comprises the amino acid sequence shown in SEQ ID NO:14.

18. The TCR of any one of claims 1, 2, 3-7, 8-17 associated with a therapeutic agent or detectable moiety.

19. A pharmaceutical composition comprising a pharmaceutically acceptable carrier, and the TCR of any one of claims 1, 2, 3-7, 8-17.

20. A pharmaceutical composition comprising a pharmaceutically acceptable carrier, and a plurality of cells having the TCR of any one of claims 1, 2, 3-7, 8-17.

21. The pharmaceutical composition of claim 20 wherein the cells are T cells.

22. The pharmaceutical composition of claim 21 wherein the T cells are CD8$^+$ T cells.

23. The TCR of any one of claims 1, 2, 3-7, 8-17 which is a recombinant TCR.

24. The TCR of any one of claims 1, 2, 3-7, 8-17 which is an isolated TCR.

* * * * *

UNITED STATES PATENT AND TRADEMARK OFFICE
CERTIFICATE OF CORRECTION

| | | |
|---|---|---|
| PATENT NO. | : 8,378,074 B2 | Page 1 of 1 |
| APPLICATION NO. | : 11/887536 | |
| DATED | : February 19, 2013 | |
| INVENTOR(S) | : Bent Karsten Jakobsen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1382 days.

Signed and Sealed this
Twenty-fourth Day of March, 2015

Michelle K. Lee
*Director of the United States Patent and Trademark Office*